US011864789B2

(12) United States Patent
Lee et al.

(10) Patent No.: US 11,864,789 B2
(45) Date of Patent: Jan. 9, 2024

(54) CALIBRATED POWER-DRIVEN SURGICAL CUTTING DEVICE

(71) Applicant: SPECTRANETICS LLC, Colorado Springs, CO (US)

(72) Inventors: Weston H. Lee, Colorado Springs, CO (US); Ryan M. Sotak, Colorado Springs, CO (US)

(73) Assignee: SPECTRANETICS LLC, Colorado Springs, CO (US)

( * ) Notice: Subject to any disclaimer, the term of this patent is extended or adjusted under 35 U.S.C. 154(b) by 357 days.

(21) Appl. No.: 17/126,328

(22) Filed: Dec. 18, 2020

(65) Prior Publication Data

US 2021/0100582 A1     Apr. 8, 2021

Related U.S. Application Data

(63) Continuation of application No. 15/942,322, filed on Mar. 30, 2018, now Pat. No. 10,932,812.

(51) Int. Cl.
*A61B 17/3207* (2006.01)
*A61B 17/32* (2006.01)
(Continued)

(52) U.S. Cl.
CPC .............. *A61B 17/320758* (2013.01); *A61B 17/00234* (2013.01); *A61B 17/32002* (2013.01); *A61B 17/320016* (2013.01); *A61B 17/32053* (2013.01); *A61N 1/05* (2013.01); *A61B 17/3468* (2013.01); *A61B 2017/00017* (2013.01); *A61B 2017/00039* (2013.01);
(Continued)

(58) Field of Classification Search
CPC ...... A61B 17/00234; A61B 17/320016; A61B 17/32002; A61B 17/32053; A61B 17/320758; A61B 17/3468; A61B 2017/00017; A61B 2017/0039; A61B 2017/00119; A61B 2017/00398; A61B 2017/00455; A61B 2017/00477; A61B 2017/00725; A61B 2017/00734; A61B 2017/320024; A61B 2090/0801; A61B 2090/0811; A61N 1/05
See application file for complete search history.

(56) References Cited

U.S. PATENT DOCUMENTS 5,651,781 A   7/1997  Grace
6,167,315 A  12/2000  Coe
(Continued)

FOREIGN PATENT DOCUMENTS

WO     2014151814 A1    9/2014

*Primary Examiner* — Mohamed G Gabr

(57) ABSTRACT

Devices for removing implanted objects from body vessels are provided. A device includes a sheath assembly having a cutting tip. The cutting tip includes a cutting surface that is adapted to cut tissue coupled to an implanted object as the cutting tip rotates. The sheath assembly further includes an outer shield carried outside of the cutting tip. The outer shield includes a distal opening, and the outer shield is translatable relative to the cutting tip from a first position to a second position and vice versa. In the first position the cutting surface of the cutting tip is disposed within the outer shield, and in the second position the cutting tip extends through the distal opening and the cutting surface is at least partially disposed outside of the outer shield.

14 Claims, 29 Drawing Sheets

(51) Int. Cl.
    *A61B 17/00*         (2006.01)
    *A61B 17/3205*     (2006.01)
    *A61N 1/05*          (2006.01)
    *A61B 90/00*       (2016.01)
    *A61B 17/34*       (2006.01)

(52) U.S. Cl.
    CPC ........... *A61B 2017/00119* (2013.01); *A61B 2017/00398* (2013.01); *A61B 2017/00455* (2013.01); *A61B 2017/00477* (2013.01); *A61B 2017/00725* (2013.01); *A61B 2017/00734* (2013.01); *A61B 2017/320024* (2013.01); *A61B 2090/0801* (2016.02); *A61B 2090/0811* (2016.02)

(56) References Cited

U.S. PATENT DOCUMENTS

| | | |
|---|---|---|
| 9,603,618 B2 | 3/2017 | Grace |
| 9,668,765 B2 | 6/2017 | Grace |
| 9,980,743 B2 | 5/2018 | Grace |
| 10,932,812 B2 * | 3/2021 | Lee ................. A61B 17/00234 |
| 2003/0125717 A1 * | 7/2003 | Whitman ............ A61B 17/068 |
| | | 606/1 |
| 2008/0154693 A1 | 6/2008 | Bateni |
| 2015/0105796 A1 | 4/2015 | Grace |
| 2015/0164530 A1 * | 6/2015 | Carver ............ A61B 17/32053 |
| | | 606/129 |
| 2016/0360947 A1 | 12/2016 | Iida |
| 2018/0221055 A1 | 8/2018 | Grace |

* cited by examiner

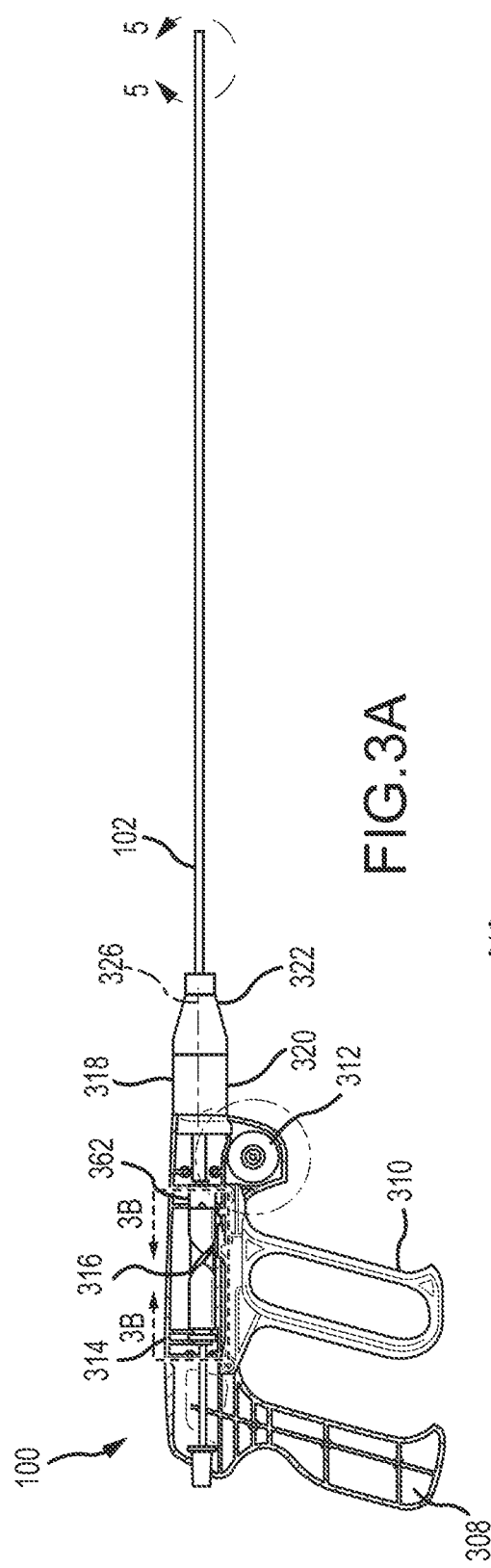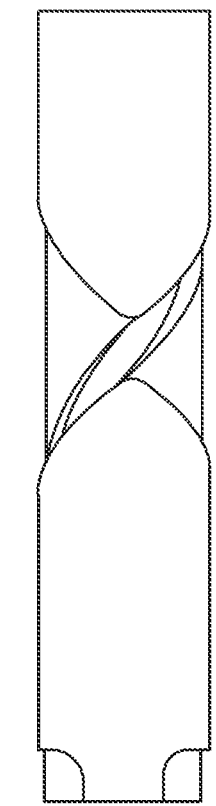
FIG.3A
FIG.3B

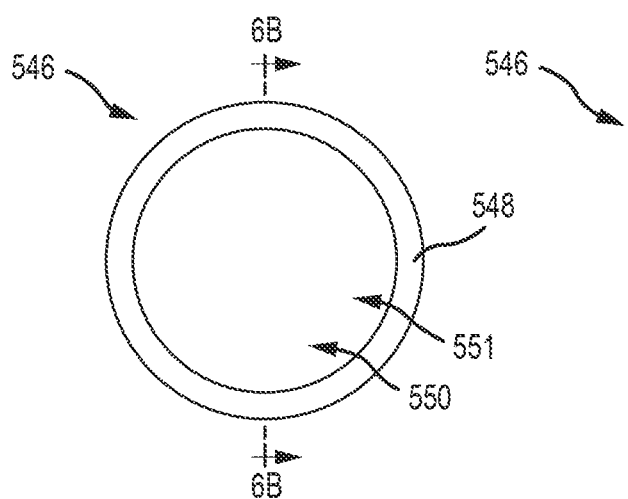
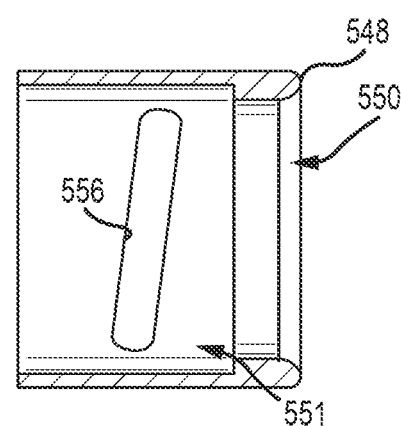
FIG.6A   FIG.6B
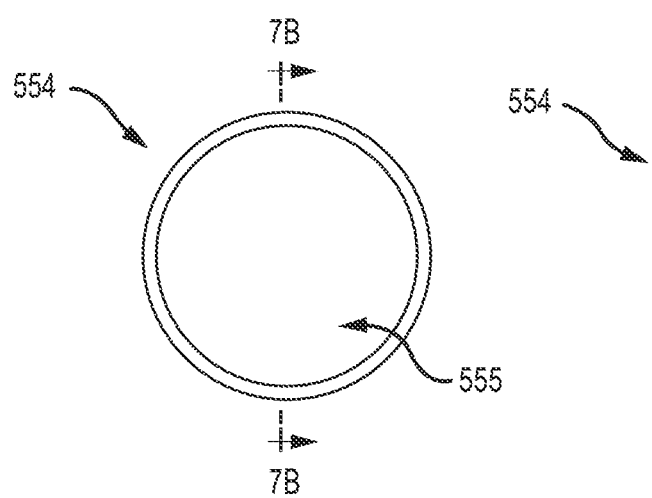
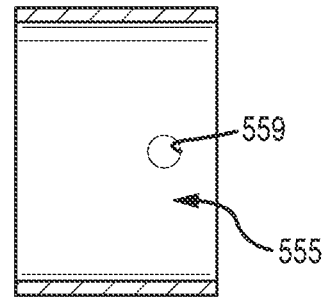
FIG.7A   FIG.7B

CALIBRATED POWER-DRIVEN SURGICAL CUTTING DEVICE

CROSS REFERENCE TO RELATED APPLICATION

The present application is a continuation of U.S. application Ser. No. 15/942,322, which is related to U.S. application Ser. No. 14/635,742, filed Mar. 2, 2015, entitled MULTIPLE CONFIGURATION SURGICAL CUTTING DEVICE, which claims the benefit of and priority to, under 35 U.S.C. § 119(e), U.S. Provisional Application Ser. No. 61/947,377, filed Mar. 3, 2014, entitled MEDICAL DEVICE FOR REMOVING AN IMPLANTED OBJECT, U.S. Provisional Application Ser. No. 61/987,993, filed May 2, 2014, entitled DUAL MODE MECHANICAL CATHETER CUTTING SYSTEM, U.S. Provisional Application Ser. No. 62/058,790, filed Oct. 2, 2014, entitled MEDICAL DEVICE FOR REMOVING AN IMPLANTED OBJECT, U.S. Provisional Application Ser. No. 62/094,808, filed Dec. 19, 2014, entitled MULTIPLE CONFIGURATION SURGICAL CUTTING DEVICE, and U.S. Provisional Application Ser. No. 62/113,865, filed Feb. 9, 2015, entitled MEDICAL DEVICE FOR REMOVING AN IMPLANTED OBJECT. The present application is also related to U.S. application Ser. No. 14/635,742, filed Mar. 2, 2015, entitled MULTIPLE CONFIGURATION SURGICAL CUTTING DEVICE, which is a continuation-in-part of commonly owned International Application No. PCT/US2014/026496, filed Mar. 13, 2014 and entitled SURGICAL INSTRUMENT FOR REMOVING AN IMPLANTED OBJECT, which claims the benefit of and priority to U.S. Provisional Application Ser. No. 61/793,597, filed Mar. 15, 2013, entitled SURGICAL INSTRUMENT FOR REMOVING AN IMPLANTED OBJECT. This patent application is also related to U.S. application Ser. No. 15/942,313, filed Mar. 30, 2018, entitled SURGICAL CUTTING DEVICE WITH SHIELD DRIVE MECHANISM. Each of the above applications is hereby incorporated herein by reference in their entireties for all that they teach and for all purposes.

FIELD OF THE DISCLOSURE

The present disclosure relates generally to devices, methods and systems for separating tissue in a patient, and more specifically, to devices for separating tissue attached to implanted objects, such as leads, in a patient and removing such objects.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat faster. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached with the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. As mentioned above, the body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature.

A variety of tools have been developed to make lead extraction safer and more successful. Current lead extraction techniques include mechanical traction, mechanical devices, and laser devices. Mechanical traction may be accomplished by inserting a locking stylet into the hollow portion of the lead and then pulling the lead to remove it. An example of such a lead locking device is described and illustrated in U.S. Pat. No. 6,167,315 to Coe et al., which is hereby incorporated herein by reference in its entirety for all that it teaches and for all purposes.

A mechanical device to extract leads includes a flexible tube called a sheath that passes over the lead and/or the surrounding tissue. The sheath typically may include a cutting blade, such that upon advancement, the cutting blade and sheath cooperate to separate the scar tissue from other scar tissue including the scar tissue surrounding the lead. In some cases, the cutting blade and sheath may also separate the tissue itself from the lead. Once the lead is separated from the surrounding tissue and/or the surrounding tissue is separated from the remaining scar tissue, the lead may be inserted into a hollow lumen of the sheath for removal and/or be removed from the patient's vasculature using some other mechanical devices, such as the mechanical traction device previously described in United States Patent Publication No. 2008/0154693 to Taylor, which is hereby incorporated herein by reference in its entirety for all that it teaches and for all purposes.

Some lead extraction devices include mechanical sheaths that have trigger mechanisms for extending the blade from the distal end of the sheath. An example of such devices and method used to extract leads is described and illustrated in U.S. Pat. No. 5,651,781 to Grace, which is hereby incorporated herein by reference in its entirety for all that it teaches and for all purposes.

Controlling the extension of the blade within a patient's vasculature may be critical, particularly when the sheath and blade negotiate tortuous paths that exist in certain vascular or physiological environments. Furthermore, in certain cases, using such mechanical devices for lead removal may require more precise control, such as when the leads are located in, and/or attached to a structurally-weak portion of the vasculature. For instance, typical leads in a human may pass through the innominate vein, past the superior vena cava ("SVC"), and into the right atrium of the heart. Tissue growth occurring along the SVC and other locations along the innominate vein may increase the risk and difficulty in extracting the leads from such locations, particularly when the vein(s)' walls are thin. Tissue growth may also occur at other challenging locations within a patient's vasculature which requires the delicate and precise control of the devices used to extract leads from such locations.

SUMMARY

A device for removing an implanted object from a body vessel in accordance with this disclosure includes an intermediate sheath assembly including an intermediate sheath and an intermediate tip disposed at a distal end of the intermediate sheath assembly; an inner sheath assembly rotatably carried within the intermediate sheath assembly, the inner sheath assembly including an inner sheath and a cutting tip, the cutting tip including a cutting surface adapted to cut tissue coupled to the implanted object as the cutting tip rotates relative to the intermediate sheath assembly; a handle assembly including a housing, a trigger carried by the housing, and a cutting tip drive mechanism carried by the housing and coupled to the trigger and the inner sheath assembly, the trigger being actuatable to drive the cutting tip drive mechanism and thereby rotate the inner sheath and the cutting tip relative to the intermediate sheath assembly; an outer sheath assembly carried outside of the intermediate sheath assembly, the outer sheath assembly including an outer sheath and an outer shield disposed at a distal end of the outer sheath assembly, the outer shield including a distal opening, the outer sheath assembly being translatable relative to the intermediate sheath assembly from a first position to a second position and vice versa, in the first position the cutting surface of the cutting tip being disposed within the outer shield, and in the second position the cutting tip extending through the distal opening and the cutting surface being at least partially disposed outside of the outer shield; and a shield drive mechanism coupled to the outer sheath assembly, the shield drive mechanism being actuatable to translate the outer sheath assembly relative to the intermediate sheath assembly from the first position to the second position and vice versa.

The device of the preceding paragraph, wherein the intermediate sheath assembly includes a longitudinal axis extending between the distal end of the intermediate sheath assembly and a proximal end of the intermediate sheath assembly, wherein the shield drive mechanism is actuated by rotating about the longitudinal axis.

The device of any of the preceding paragraphs, wherein the trigger is actuated by proximally and distally translating the trigger relative to the housing.

The device of any of the preceding paragraphs, wherein the shield drive mechanism is rotatably coupled to the housing of the handle assembly.

The device of any of the preceding paragraphs, wherein the shield drive mechanism is actuated to rotate the outer sheath assembly relative to the intermediate sheath assembly, and further including a cam and follower mechanism defined by the intermediate tip and the outer shield, the cam and follower mechanism translating the outer sheath assembly relative to the intermediate sheath assembly from the first position to the second position and vice versa when the outer sheath assembly rotates relative to the intermediate sheath assembly.

The device of any of the preceding paragraphs, wherein the cam and follower mechanism is a first cam and follower mechanism, and further including a second cam and follower mechanism defined by the intermediate tip and the cutting tip, the second cam and follower mechanism translating the cutting tip relative to the intermediate tip as the cutting tip rotates relative to the intermediate tip.

The device of any of the preceding paragraphs, further including a cam and follower mechanism defined by the intermediate tip and the cutting tip, the cam and follower mechanism translating the cutting tip relative to the intermediate tip as the cutting tip rotates relative to the intermediate tip.

The device of any of the preceding paragraphs, wherein in the first position of the outer shield, the cutting surface of the cutting tip remains disposed within the outer shield when the cam and follower mechanism translates the cutting tip relative to the intermediate tip as the cutting tip rotates relative to the intermediate tip.

The device of any of the preceding paragraphs, wherein the intermediate sheath assembly includes a longitudinal axis extending between the distal end of the intermediate sheath assembly and a proximal end of the intermediate sheath assembly, and the cutting surface of the cutting tip is perpendicular relative to the longitudinal axis.

The device of any of the preceding paragraphs, wherein the intermediate sheath assembly includes a longitudinal axis extending between the distal end of the intermediate sheath assembly and a proximal end of the intermediate sheath assembly, and the cutting surface of the cutting tip is disposed at an acute angle relative to the longitudinal axis.

The device of any of the preceding paragraphs, wherein the cutting tip drive mechanism includes a barrel cam coupled to the trigger and the inner sheath assembly, the trigger being actuatable to rotate the barrel cam and thereby rotate the inner sheath and the cutting tip relative to the intermediate sheath assembly.

The device of any of the preceding paragraphs, wherein the barrel cam includes a cam slot that extends longitudinally and circumferentially on the barrel cam, and the cam slot couples the barrel cam to the trigger.

A device for removing an implanted object from a body vessel in accordance with this disclosure includes an intermediate sheath assembly including an intermediate sheath and an intermediate tip disposed at a distal end of the intermediate sheath assembly; an inner sheath assembly rotatably carried within the intermediate sheath assembly, the inner sheath assembly including an inner sheath and a cutting tip, the cutting tip including a cutting surface adapted to cut tissue coupled to the implanted object as the cutting tip rotates relative to the intermediate sheath assembly; a handle assembly including a housing, a trigger carried by the housing, and a cutting tip drive mechanism carried by the housing and coupled to the trigger and the inner sheath assembly, the trigger being actuatable to drive the cutting tip drive mechanism and thereby rotate the inner sheath and the cutting tip relative to the intermediate sheath assembly; an outer shield carried outside of the intermediate tip, the outer shield including a distal opening, the outer shield being translatable relative to the intermediate tip from a first position to a second position and vice versa, in the first position the cutting surface of the cutting tip being disposed within the outer shield, and in the second position the cutting tip extending through the distal opening and the cutting surface being at least partially disposed outside of the outer shield; and a cam and follower mechanism defined by the intermediate tip and the outer shield, the cam and follower mechanism translating the outer shield relative to the intermediate tip from the first position to the second position and vice versa upon rotation of the outer shield relative to the intermediate tip.

The device of the preceding paragraph, wherein the cam and follower mechanism is a first cam and follower mechanism, and further including a second cam and follower mechanism defined by the intermediate tip and the cutting tip, the second cam and follower mechanism translating the cutting tip relative to the intermediate tip as the cutting tip rotates relative to the intermediate tip.

A device for removing an implanted object from a body vessel in accordance with this disclosure includes an inner sheath assembly including an inner sheath and a cutting tip disposed at a distal end of the inner sheath assembly, the cutting tip including a cutting surface adapted to cut tissue coupled to the implanted object as the cutting tip rotates; a handle assembly including a housing, a trigger carried by the housing, and a cutting tip drive mechanism carried by the housing and coupled to the trigger and the inner sheath assembly, the trigger being actuatable to drive the cutting tip drive mechanism and thereby rotate the inner sheath and the cutting tip relative to the housing; an outer sheath assembly carried outside of the inner sheath assembly, the outer sheath assembly including an outer sheath and an outer shield disposed at a distal end of the outer sheath assembly, the outer shield including a distal opening, the outer sheath assembly being translatable relative to the inner sheath assembly from a first position to a second position and vice versa, in the first position the cutting surface of the cutting tip being disposed within the outer shield, and in the second position the cutting tip extending through the distal opening and the cutting surface being at least partially disposed outside of the outer shield; and a shield drive mechanism coupled to the outer sheath assembly, the shield drive mechanism being actuatable to translate the outer sheath assembly relative to the inner sheath assembly from the first position to the second position and vice versa.

The device of the preceding paragraph, wherein the inner sheath assembly includes a longitudinal axis extending between the distal end of the inner sheath assembly and a proximal end of the inner sheath assembly, wherein the shield drive mechanism is actuated by rotating about the longitudinal axis.

The device of any of the preceding paragraphs, wherein the trigger is actuated by proximally and distally translating the trigger relative to the housing.

The device of any of the preceding paragraphs, wherein the shield drive mechanism is rotatably coupled to the housing of the handle assembly.

The device of any of the preceding paragraphs, wherein the cutting tip rotates about the longitudinal axis.

The device of any of the preceding paragraphs, wherein the cutting surface of the cutting tip and the distal opening of the outer shield are disposed perpendicularly relative to the longitudinal axis.

The device of any of the preceding paragraphs, wherein the shield drive mechanism is actuated to rotate and translate the outer sheath assembly relative to the inner sheath assembly from the first position to the second position and vice versa.

A device for removing an implanted object from a body vessel in accordance with this disclosure includes an outer sheath; an outer cam member coupled to the outer sheath; an intermediate sheath carried within the outer sheath; an intermediate cam member coupled to the intermediate sheath and carried within the outer cam member, the intermediate cam member comprising a first cam slot; a first pin received in the first cam slot and connecting the intermediate cam member to the outer cam member; an inner sheath carried within the intermediate sheath; an inner cam member coupled to the inner sheath and carried within the intermediate cam member, the inner cam member comprising a cutting surface and a second cam slot; a second pin received in the second cam slot and connecting the inner cam member to the intermediate cam member.

A device for removing an implanted object from a body vessel, the device comprising an outer sheath assembly comprising an outer sheath and an outer shield disposed adjacent a distal end of the outer sheath, the outer shield comprising a shield distal end, an inner sheath assembly disposed within the outer sheath assembly, the inner sheath assembly comprising an inner sheath and a cutting tip disposed adjacent a distal end of the inner sheath, wherein the cutting tip has a cutting surface, a shield drive mechanism coupled to the outer sheath assembly, the shield drive mechanism comprising a knob and a button, whereupon actuation of the button, the knob is able to rotate, thereby rotating and translating the outer shield from a first position to a second position and vice versa, wherein the outer shield is more distal in the second position relative to the first position, a translation mechanism for translating the cutting tip relative to the distal end of the outer sheath, and a cutting tip drive mechanism for rotating the cutting tip, the cutting tip drive mechanism coupled to the translation mechanism, whereupon actuation of the cutting tip drive mechanism, the cutting tip rotates and translates and (a) remains proximal of the shield distal end when the outer shield is in the second position and (b) extends distally of the shield distal end when the shield is in the first position.

The device of device of the preceding paragraph, the shield drive mechanism further comprising a sealing material.

The device of any of the preceding paragraphs, wherein the sealing material comprises an elastomeric material.

The device of any of the preceding paragraphs, wherein the foam is foam.

The device of any of the preceding paragraphs, wherein at least a portion of the sealing material is disposed between the knob and at least one of the inner sheath, the outer sheath and an intermediate sheath, wherein the intermediate sheath is disposed between the inner sheath and the outer sheath.

The device of any of the preceding paragraphs, wherein at least a portion of the sealing material is disposed between the knob and the intermediate sheath.

The device of any of the preceding paragraphs, further comprising a housing, wherein the shield drive mechanism is rotatably coupled to the housing, and the shield drive mechanism is actuated by rotating the knob about a longitudinal axis of the outer sheath assembly.

The device of any of the preceding paragraphs, further comprising a trigger carried by the housing, wherein the trigger is actuated by translating the trigger relative to the housing.

The device of any of the preceding paragraphs, further comprising a sealing material disposed between the trigger and the housing.

The device of any of the preceding paragraphs, wherein the sealing material comprises foam.

The device of any of the preceding paragraphs, wherein the foam is an open-cell foam.

The device of any of the preceding paragraphs, wherein the foam is a closed-cell foam.

The device of any of the preceding paragraphs, further comprising a cam and follower mechanism coupling the outer shield to the intermediate sheath assembly, wherein the cam and follower mechanism translate the outer sheath assembly relative to the inner sheath assembly from the first position to the second position and vice versa upon rotation of the knob.

The device of any of the preceding paragraphs, wherein the inner sheath assembly comprises a longitudinal axis extending between the distal end of the inner sheath assembly and a proximal end of the inner sheath assembly, wherein the cutting tip rotates about the longitudinal axis.

The device of any of the preceding paragraphs, further comprising an electric motor.

The device of any of the preceding paragraphs, further comprising a power supply electrically coupled to the electric motor.

The device of any of the preceding paragraphs, wherein the power supply is a battery.

The device of any of the preceding paragraphs, further comprising one or more gears coupling the electric motor to the inner sheath assembly.

The device of any of the preceding paragraphs, further comprising a sealing material disposed between at least one of the battery and motor and at least one of the inner sheath, the outer sheath and an intermediate sheath, wherein the intermediate sheath is disposed between the inner sheath and the outer sheath.

The device of any of the preceding paragraphs, wherein the sealing material comprises an elastomeric material.

A device for removing an implanted object from a body vessel, the device comprising an outer sheath comprising a shield distal end, an inner sheath disposed within the outer sheath, the inner sheath comprising a cutting tip having a cutting surface, a shield drive mechanism coupled to the outer sheath, wherein the shield drive mechanism is configured to move the outer shield from a first position to a second position and vice versa, wherein the outer shield is more distal in the second position relative to the first position, a cutting tip drive mechanism for rotating the cutting tip, whereupon actuation of the cutting tip drive mechanism, the cutting tip rotates and translates and (a) remains proximal of the shield distal end when the outer shield is in the second position and (b) extends distally of the shield distal end when the outer shield is in the first position, a sensor, wherein the sensor provides a position signal indicative of the cutting tip being in at least one of a non-extended position and an extended position, and a controller comprising non-transitory computer-readable medium containing instructions that, when executed, cause one or more processors to present an alert, via an interface, upon receiving the position signal, wherein the alert is indicative of the cutting tip being in at least one of the non-extended position and the extended position.

The device of the preceding paragraph, wherein the alert is at least one of an audible signal, a visual signal, and a tactile signal.

The device of any of the preceding paragraphs, wherein the alert is at least two of an audible signal, a visual signal, and a tactile signal.

The device of any of the preceding paragraphs, wherein the alert comprises an audible signal and a visual signal.

The device of any of the preceding paragraphs, wherein the non-transitory computer-readable medium contains further instructions that, when executed, allow the controller to initiate activation of the cutting tip drive mechanism upon the position signal being indicative of the cutting tip being in at least one of the non-extended position and the extended position.

The device of any of the preceding paragraphs, wherein the non-transitory computer-readable medium contains further instructions that, when executed, allow the controller to initiate activation of the cutting tip drive mechanism upon the position signal being indicative of the cutting tip being in the non-extended position.

The device of any of the preceding paragraphs, further comprising a second sensor, wherein the second sensor provides a shield position signal indicative of the outer shield being in at least one of the first position and the second position.

The device of any of the preceding paragraphs, wherein the non-transitory computer-readable medium contains further instructions that, when executed, allow the controller to initiate activation of the cutting tip drive mechanism upon the shield position signal being indicative of the outer shield being in at least one of the first position and the second position.

The device of any of the preceding paragraphs, wherein the non-transitory computer-readable medium contains further instructions that, when executed, allow the controller to initiate activation of the cutting tip drive mechanism upon the shield position signal being indicative of the outer shield being in the second position.

The device of any of the preceding paragraphs, wherein the non-transitory computer-readable medium contains further instructions that, when executed, deactivates the controller from initiating activation of the cutting tip drive mechanism upon the position signal being indicative of the cutting tip being in at least one of the non-extended position and the extended position.

The device of any of the preceding paragraphs, wherein the non-transitory computer-readable medium contains further instructions that, when executed, deactivates the controller from initiating activation of the cutting tip drive mechanism upon the position signal being indicative of the cutting tip being in the extended position.

The device of any of the preceding paragraphs, wherein the non-transitory computer-readable medium contains further instructions that, when executed, allow the controller to initiate activation of the cutting tip drive mechanism upon the position signal being indicative of the cutting tip being in at least one of the non-extended position and the extended position.

The device of any of the preceding paragraphs, wherein the non-transitory computer-readable medium contains further instructions that, when executed, allow the controller to initiate activation of the cutting tip drive mechanism upon the position signal being indicative of the cutting tip being in the non-extended position.

The device of any of the preceding paragraphs, further comprising a second sensor, wherein the second sensor provides a shield position signal indicative of the outer shield being in at least one of the first position and the second position.

A device for removing an implanted object from a body vessel, the device comprising an outer sheath comprising a shield distal end, an inner sheath disposed within the outer sheath, the inner sheath comprising a cutting tip having a cutting surface, a shield drive mechanism coupled to the outer sheath, wherein the shield drive mechanism is configured to move the outer shield from a first position to a second position and vice versa, wherein the outer shield is more distal in the second position relative to the first position, a sensor, wherein the sensor provides a position signal indicative of the outer shield being in a at least one of the first position or the second position, and a cutting tip drive mechanism for rotating the cutting tip, whereupon actuation of the cutting tip drive mechanism, the cutting tip rotates and translates and (a) remains proximal of the shield distal end when the outer shield is in the second position and (b) extends distally of the shield distal end when the outer shield is in the first position, and a controller comprising non-transitory computer-readable medium containing instructions that, when executed, cause one or more processors to present an alert, via an interface, upon receiving the position signal, wherein the alert is indicative of the outer shield being in a at least one of the first position or the second position.

The device of the preceding paragraph, wherein the alert is at least one of an audible signal, a visual signal, and a tactile signal.

The device of any of the preceding paragraphs, wherein the alert is at least two of an audible signal, a visual signal, and a tactile signal.

The device of any of the preceding paragraphs, wherein the alert comprises an audible signal and a visual signal.

The device of any of the preceding paragraphs, wherein the non-transitory computer-readable medium contains further instructions that, when executed, allow the controller to initiate activation of the cutting tip drive mechanism upon the position signal being indicative of the outer shield being in at least one of the first position or the second position. The device of any of the preceding paragraphs, wherein the non-transitory computer-readable medium contains further instructions that, when executed, allow the controller to initiate activation of the cutting tip drive mechanism upon the position signal being indicative of the outer shield being in the second position.

The device of any of the preceding paragraphs, further comprising a second sensor, wherein the second sensor provides a tip position signal indicative of the cutting tip being in at least one of a non-extended position and an extended position.

The device of any of the preceding paragraphs, wherein the non-transitory computer-readable medium contains further instructions that, when executed, allow the controller to initiate activation of the cutting tip drive mechanism upon the tip position signal being indicative of the cutting tip being in at least one of a non-extended position and an extended position.

The device of any of the preceding paragraphs, wherein the non-transitory computer-readable medium contains further instructions that, when executed, allow the controller to initiate activation of the cutting tip drive mechanism upon the tip position signal being indicative of cutting tip being in the non-extended position.

The device of any of the preceding paragraphs, wherein the non-transitory computer-readable medium contains further instructions that, when executed, deactivates the controller from initiating activation of the cutting tip drive mechanism upon the position signal being indicative of the outer shield being in at least one of the first position or the second position.

The device of any of the preceding paragraphs, wherein the non-transitory computer-readable medium contains further instructions that, when executed, deactivates the controller from initiating activation of the cutting tip drive mechanism upon the position signal being indicative of the outer shield being in the second position.

A device for removing an implanted object from a body vessel, the device comprising an outer sheath comprising a shield distal end, an inner sheath disposed within the outer sheath, the inner sheath comprising a cutting tip having a cutting surface, a cutting tip drive mechanism for rotating the cutting tip, a sensor, wherein the sensor provides a power signal indicative of at least one of power, force and current applied to rotate the cutting tip, and a controller comprising non-transitory computer-readable medium containing instructions that, when executed, cause one or more processors to affect rotation of the cutting tip based upon the power signal and the first power threshold.

The device of the preceding paragraph, wherein the controller further comprises instructions that present an alert, via an interface, upon the power signal satisfying the first power threshold.

The device of any of the preceding paragraphs, wherein the non-transitory computer-readable medium contains further instructions that, when executed, allow the controller to initiate activation of the cutting tip drive mechanism upon the power signal failing to satisfy the first power threshold.

The device of any of the preceding paragraphs, wherein the non-transitory computer-readable medium contains further instructions that, when executed, deactivates the cutting tip drive mechanism upon the power signal satisfying the first power threshold.

The device of any of the preceding paragraphs, further comprising a shield position sensor, wherein the shield position sensor provides a shield position signal indicative of the outer shield being in at least one of the first position or the second position.

The device of any of the preceding paragraphs, wherein the non-transitory computer-readable medium contains further instructions that, when executed, deactivates the cutting tip drive mechanism upon the shield position signal being indicative of the outer shield being in at least one of the first position or the second position.

The device of any of the preceding paragraphs, further comprising a tip position sensor, wherein the tip position sensor provides a tip position signal indicative of the cutting tip being in at least one of a non-extended position and an extended position.

The device of any of the preceding paragraphs, wherein the non-transitory computer-readable medium contains further instructions that, when executed, deactivates the cutting tip drive mechanism upon the tip position signal being indicative of the cutting tip being in at least one of a non-extended position and an extended position.

The device of any of the preceding paragraphs, further comprising a tip position sensor, wherein the tip position sensor provides a tip position signal indicative of the cutting tip being in at least one of a non-extended position and an extended position.

The device of any of the preceding paragraphs, wherein the non-transitory computer-readable medium contains further instructions that, when executed, deactivates the cutting tip drive mechanism upon the tip position signal being indicative of the cutting tip being in at least one of a non-extended position and an extended position.

The device of any of the preceding paragraphs, further comprising a shield position sensor, wherein the shield position sensor provides a shield position signal indicative of the outer shield being in at least one of the first position or the second position.

The device of any of the preceding paragraphs, wherein the non-transitory computer-readable medium contains further instructions that, when executed, deactivates the cutting tip drive mechanism upon the shield position signal being indicative of the outer shield being in at least one of the first position or the second position.

The device of any of the preceding paragraphs, wherein the cutting tip drive mechanism comprises a prime mover.

The device of any of the preceding paragraphs, wherein the prime mover comprises an electric motor.

The device of any of the preceding paragraphs, further comprising a power supply electrically coupled to the electric motor.

The device of any of the preceding paragraphs, wherein the power supply is a battery.

A device for removing an implanted object from a body vessel, the device comprising an outer sheath, an inner sheath disposed within the outer sheath, the inner sheath comprising a cutting tip having a cutting surface, a cutting tip drive mechanism for rotating the cutting tip, whereupon actuation of the cutting tip drive mechanism, the cutting tip rotates and translates, wherein the cutting tip drive mechanism includes a motor and motor encoder, a sensor, wherein the sensor provides a position signal indicative of a home position for the cutting tip drive mechanism, and a controller comprising non-transitory computer-readable medium containing instructions that, when executed, cause one or more processors to calibrate the motor encoder based at least in part on the position signal.

The device of the preceding paragraph, wherein the non-transitory computer-readable medium contains further instructions that, when executed, allow the controller to initiate activation of the cutting tip drive mechanism upon calibrating the motor encoder.

The device of any of the preceding paragraphs, wherein the instructions to calibrate the motor encoder comprise rotating the motor in one direction.

The device of any of the preceding paragraphs, wherein the instructions to calibrate the motor encoder comprise rotating the motor in the one direction until the sensor produces the position signal.

The device of any of the preceding paragraphs, wherein the instructions to calibrate the motor encoder comprise discontinuing rotating the motor in one direction.

The device of any of the preceding paragraphs, wherein the instructions to calibrate the motor encoder comprise discontinuing rotating the motor in one direction and rotating the motor in an opposite direction.

The device of any of the preceding paragraphs, wherein the instructions to calibrate the motor encoder comprise rotating the motor in the opposition direction until the sensor produces the position signal.

The device of any of the preceding paragraphs, wherein the cutting tip drive mechanism further comprises a current sensor, wherein the current sensor produces a current signal indicative of the motor exceeding a predetermined current threshold.

The device of any of the preceding paragraphs, wherein the instructions discontinue rotating the motor in one direction based upon the current signal exceeding the predetermined current threshold.

The device of any of the preceding paragraphs, wherein the instructions to calibrate the motor encoder comprise rotating the motor in the opposition direction.

The device of any of the preceding paragraphs, wherein the instructions to calibrate the motor encoder comprise rotating the motor in the opposition direction until the sensor produces the position signal.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (for example, X1 and X2) as well as a combination of elements selected from two or more classes (for example, Y1 and Zo).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

A "lead" is a conductive structure, typically an electrically insulated coiled wire. The electrically conductive material may be any conductive material, with metals and intermetallic alloys common. The outer sheath of insulated material is biocompatible and bio stable (for example, non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "module" or "logic" as used herein refers to any known or later developed hardware, software, firmware, artificial intelligence, fuzzy logic, or combination of hardware and software that is capable of performing the functionality associated with that element. Also, while the disclosure is presented in terms of exemplary embodiments, it should be appreciated that individual aspects of the disclosure can be separately claimed.

A "serration" or "serrated edge" or "serrated blade" or other variations, as used herein, shall mean the configuration of a cutting surface having a notched edge or saw-like teeth. The notched edges create a plurality of smaller points that contact (and therefore less contact area with) the material being cut in comparison to an un-notched blade. Additionally, the pressure applied by each serrated point of contact is relatively greater and the points of contact are at a sharper angle to the material being cut. One example of a serrated blade may include one notch adjacent to and abutting another notch such that there is very little, if any, blade between such notches, thereby creating points of contact. There are multiple variations and/or features of serrations. For example, one type of serrated feature is referred to as a "crown." As used herein, a serrated blade, or other variation, in the shape of a "crown," shall mean a blade comprising a plurality of notches and adjacent un-notched areas such that the combination of notched and un-notched areas resembles a crown for a royal member (for example, king, queen, etc.), particularly when the blade is circular. A further type of "crown" includes a "hook crown." As used herein, a serrated blade, or other variation, in the shape of a "hook crown," shall mean a blade comprising a plurality of notches and adjacent un-notched areas, wherein the length of un-notched areas of the blade are longer than the notched areas of the blade.

A "surgical implant" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 3A is an internal view of a handle assembly of the surgical device illustrated in FIG. 1;

FIG. 3B is a detail view of the handle assembly within line 3B-3B of FIG. 3A;

FIG. 6A is an end view of the outer shield of the surgical device illustrated in FIG. 1;

FIG. 6B is a longitudinal sectional view of the outer shield illustrated in FIG. 6A taken along line 6B-6B;

FIG. 7A is an end view of an intermediate tip of the surgical device illustrated in FIG. 1;

FIG. 7B is a longitudinal sectional view of the intermediate tip illustrated in FIG. 7A taken along line 7B-7B;

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
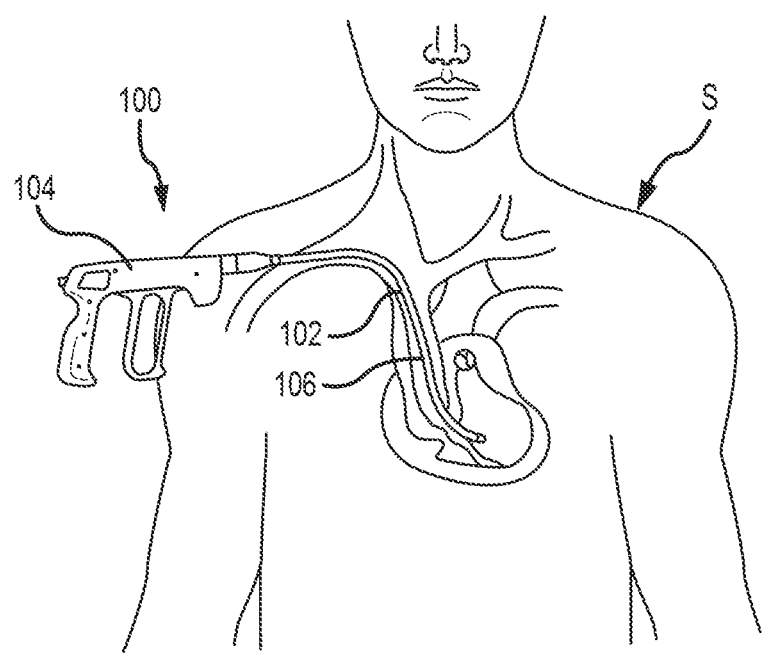
FIG. 1 is a perspective view of a subject having a pacemaker lead located in the venous system and a terminating electrode anchored to the ventricular heart chamber, with an embodiment of a surgical device being shown inserted into the body and partly advanced over the lead.
Figure 2:
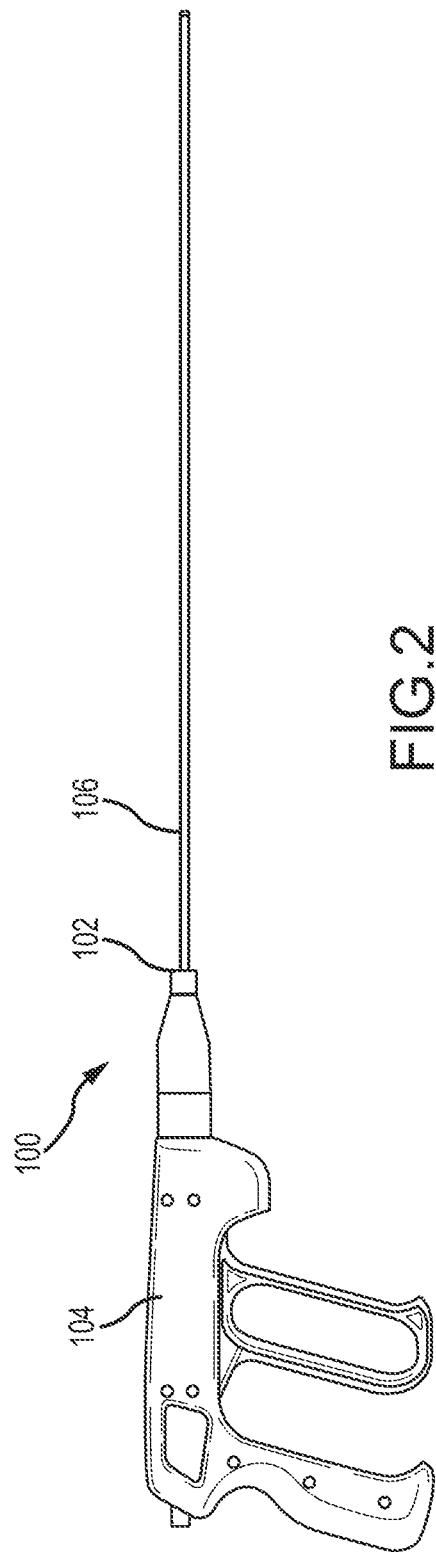
FIG. 2 is an elevation view of the surgical device illustrated in FIG. 1.

Embodiments according to this disclosure provide a surgical device that includes a sheath assembly, which can be deployed safely within a vascular system of a patient and separate implanted objects, such as leads, from a patient's vasculature system. FIGS. 1 and 2 depict a surgical device 100 having a sheath assembly 102 that is adapted to be inserted within a subject 10 (for example, a human patient). The sheath assembly 102 surrounds an implanted lead (not shown) running along the left innominate vein past the SVC and connected into, or about, the right ventricle of the heart.

Upon surrounding the lead with the sheath assembly 102, the user of the surgical device 100 (that is, a physician) may actuate a handle assembly 104, thereby rotating a cutting tip (not shown in FIG. 1) disposed at the distal end of the sheath assembly 102 to cut, separate, and/or dilate the tissue surrounding the lead within the patient's SVC.

The cutting tip may rotate to cut, separate, and/or dilate tissue in one or more shielded configurations of the device 100 in which the cutting tip is disposed within an outer sheath assembly 106 of the sheath assembly 102. In some embodiments, the shielded configuration(s) of the device 100 may inhibit the cutting tip from contacting and potentially damaging the SVC of the subject. The cutting tip may also rotate to cut, separate, and/or dilate tissue in one or more extended configurations of the device 100 in which the cutting tip at least partially protrudes from the outer sheath assembly 106. In some embodiments, the cutting tip may cut tissue more efficiently in the extended configuration(s) compared to the shielded configuration(s). As described in further detail below, the surgical device 100 is selectively reconfigurable to move the cutting tip from the shielded configuration(s) to the extended configuration(s) and vice versa. The process of rotating the cutting tip is repeated (in the shielded configuration(s) and/or the extended configuration(s)) until the implanted lead and/or surrounding tissue is completely or substantially cut, separated, and/or dilated from the tissue attached to the SVC. At that time, the implanted lead may safely be removed from the patient's SVC.

Referring to FIGS. 3A and 3B, an internal view of the handle assembly 104 is illustrated. The handle assembly 104 includes a housing 308. The housing 308 may be formed of various appropriate materials, such as polymers and the like. In some embodiments, the housing 308 includes two or more components that are coupled to one another, for example, via fasteners, adhesives, or the like. In the embodiment illustrated in FIG. 3A, the housing 308 includes two "halves", or components that are generally mirror images of each other, which together define the housing 308. In FIG. 3A, one of the halves of the housing 308 is omitted to illustrate components that are carried by the housing 308.

The housing 308 movably carries a trigger 310. The trigger 310 is actuated by the user, or moved relative to the housing 308, to cause the cutting tip to rotate. In some embodiments and as illustrated in the figures, the trigger 310 is actuated by translating the trigger 310 proximally and distally relative to the housing 308. In some embodiments, the trigger 310 may be actuated by pivoting the trigger 310 relative to the housing 308. In some embodiments, the trigger 310 may be actuated by translating and pivoting the trigger 310 relative to the housing 308. In some embodiments, the trigger 310 may be formed as a depressible button. The trigger 310 may be formed of various appropriate materials, such as polymers and the like. In some embodiments and as illustrated in the figures, the trigger 310 includes one opening into which the user can insert one or more fingers. In some embodiments, the trigger 310 may include two or more openings. In some embodiments, the trigger 310 may be a straight or non-linear member without any openings. The trigger 310 may have a variety of sizes and shapes provided that the trigger 310, either alone or in conjunction with the housing 308, is ergonomically correct and comfortable for the user.

The housing 308 of the handle assembly 104 also movably carries a spring 312. The spring 312 is coupled to the trigger 310 to urge the trigger 310 toward a home position. In some embodiments and as illustrated in the figures, the trigger 310 is actuated when the user translates the trigger 310 proximally relative to the housing 308 and the spring 312 subsequently translates the trigger 310 distally relative to the housing 308. In some embodiments and as illustrated in the figures, the spring 312 is a constant force spring.

The housing 308 of the handle assembly 104 further carries a cutting tip drive mechanism 314 that is coupled to the sheath assembly 102. Actuation of the trigger 310 drives the cutting tip drive mechanism 314, and the cutting tip drive mechanism 314 in turn transmits rotational motion to the sheath assembly 102 and the cutting tip. In some embodiments and as illustrated in the figures, the cutting tip drive mechanism 314 includes a barrel cam 316, such as any of the barrel cams or barrel cam assemblies described and/or illustrated in U.S. Provisional Patent Application Nos. 62/058,790, 62/113,865, and/or 61/947,377, which are hereby incorporated by reference in their entirety for all they teach and for all purposes. Generally, the barrel cam 316 includes a cam slot that receives a pin carried by the trigger 310. The cam slot extends longitudinally and circumferentially on the surface of the barrel cam 316. As a result, actuation of the trigger 310, and the trigger pin, causes rotation of the barrel cam 316. The barrel cam 316 in turn transmits rotational motion to the sheath assembly 102 and the cutting tip.

The cutting tip drive mechanism 314 may take various other forms. For example, in some embodiments, the cutting tip drive mechanism 314 may be formed as a gear mechanism (not shown) or a threaded nut and shaft mechanism (not shown), such as any of the mechanisms described and/or illustrated in PCT Application No. PCT/US2014/026496, which is hereby incorporated by reference in its entirety for all it teaches and for all purposes. As another example, in some embodiments, the cutting tip drive mechanism 314 may include a prime mover (not shown), such as an electric motor, that receives power from a power supply (not shown), such as a battery carried by the housing 308.

Figure 4A:
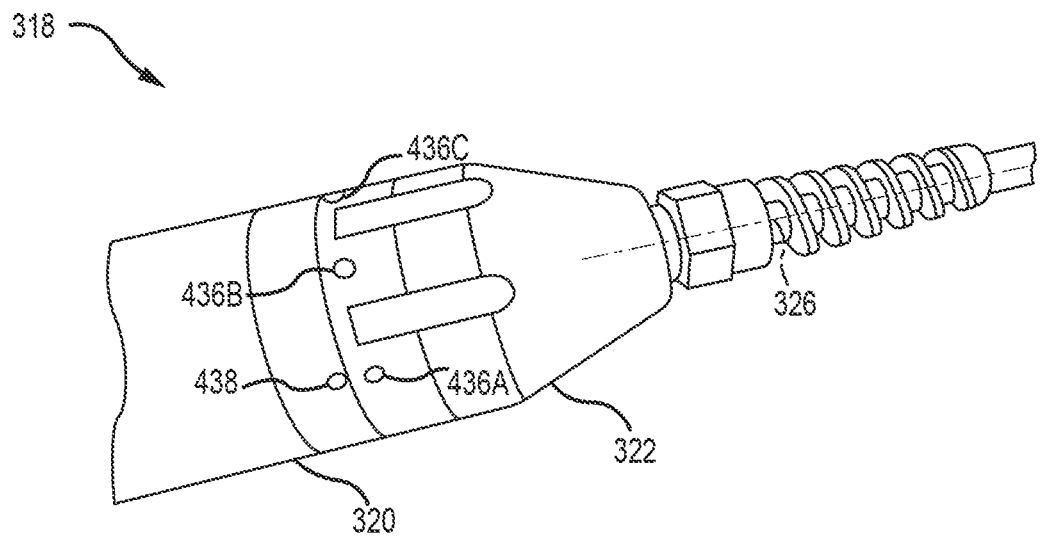
FIG. 4A is a perspective view of a shield drive mechanism of the surgical device illustrated in FIG. 1.
Figure 4B:
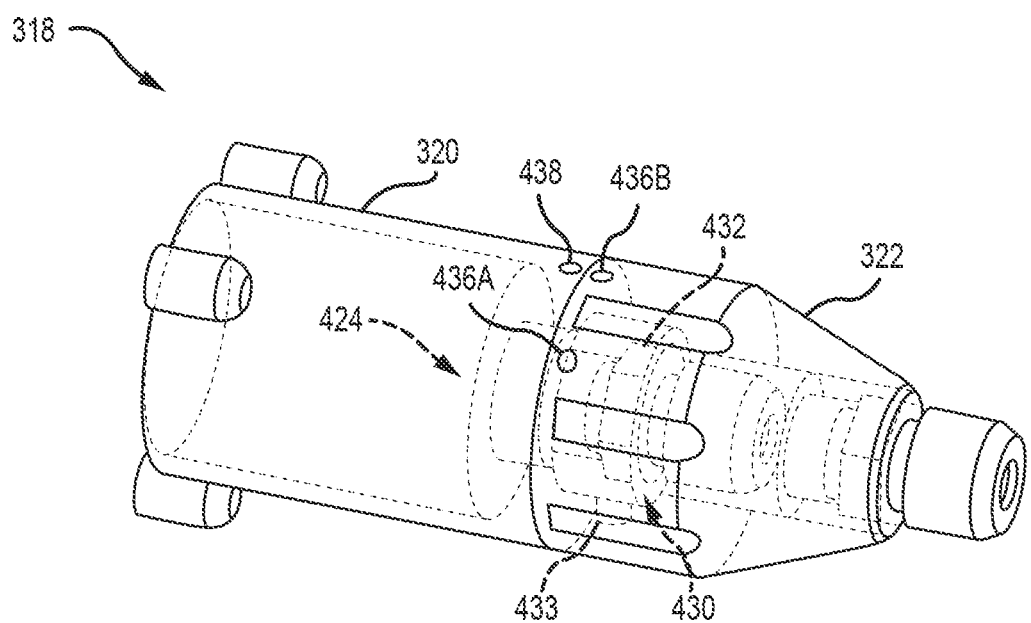
FIG. 4B is another perspective view of the shield drive mechanism of FIG. 4A.
Figure 5A:
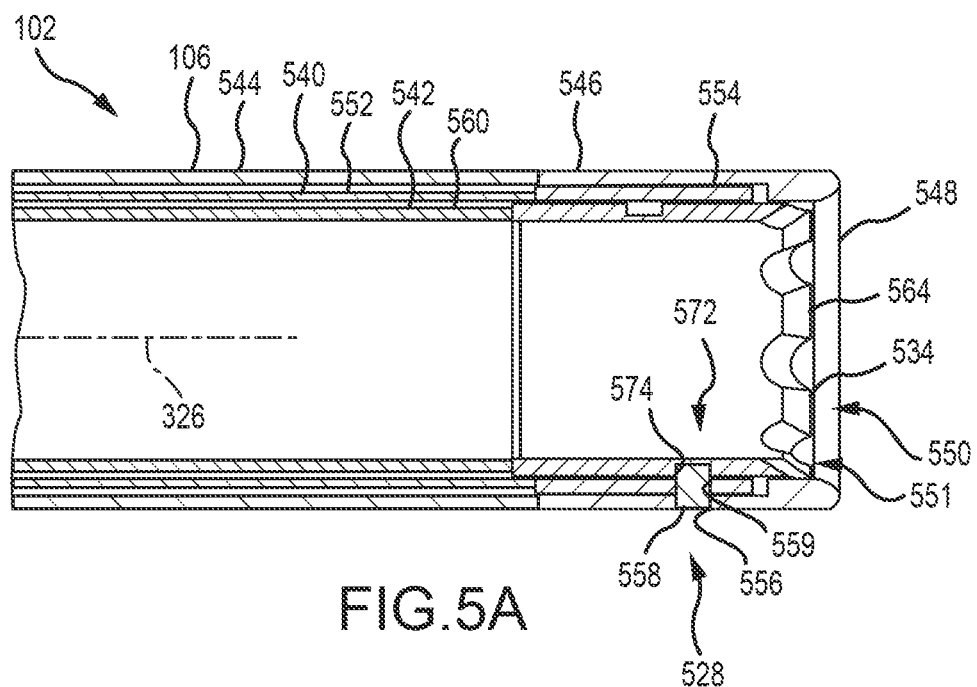
FIG. 5A is a detail, longitudinal sectional view of a sheath assembly of the surgical device within line 5-5 of FIG. 3A.
Figure 5B:
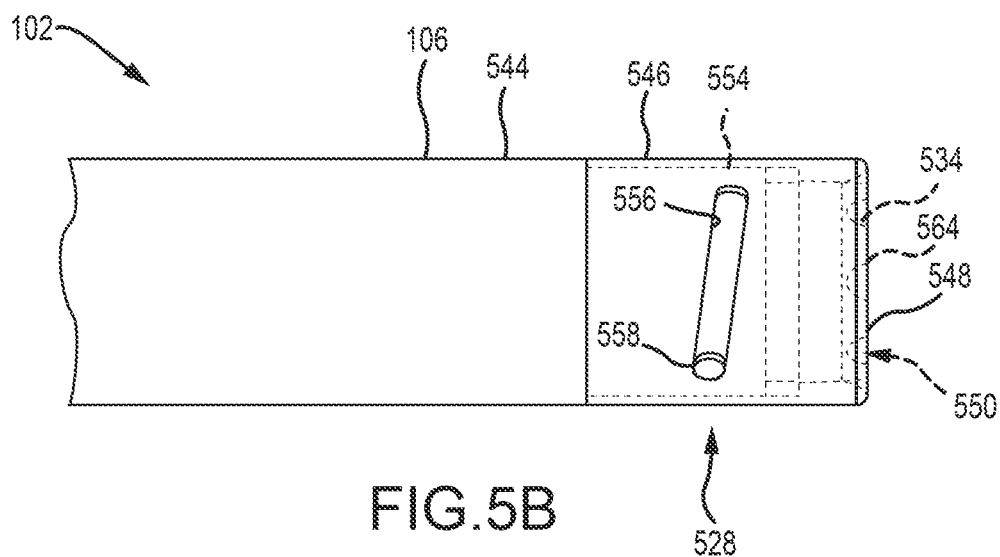
FIG. 5B is another detail view of the sheath assembly of the surgical device within line 5-5 of FIG. 3A; the surgical device is illustrated in a shielded configuration in which a cutting tip is disposed within an outer shield.
Figure 5C:
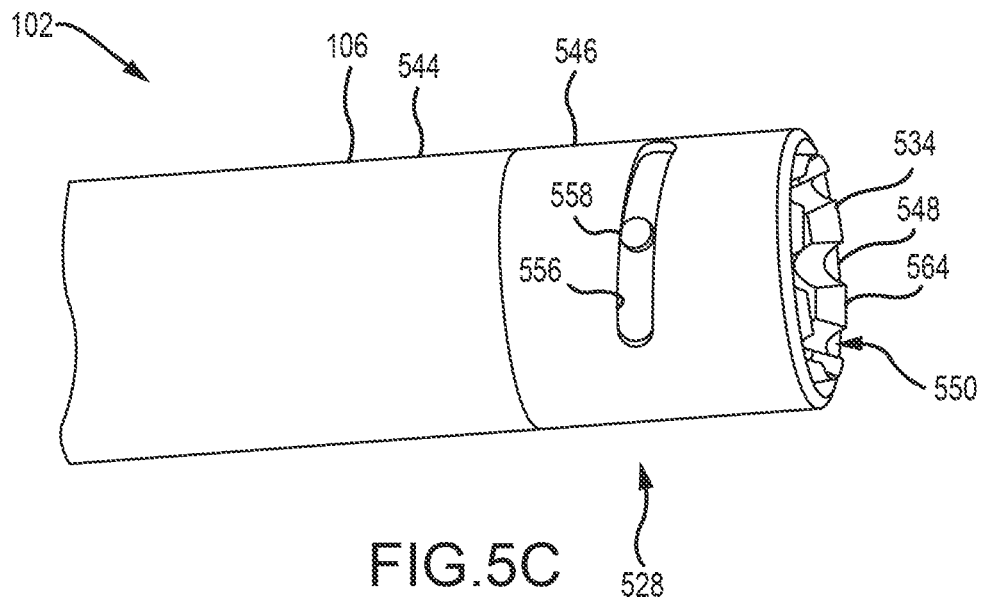
FIG. 5C is another detail view of the sheath assembly of the surgical device within line 5-5 of FIG. 3A; the surgical device is illustrated in a first extended configuration in which the cutting tip partially protrudes from the outer shield.
Figure 5D:
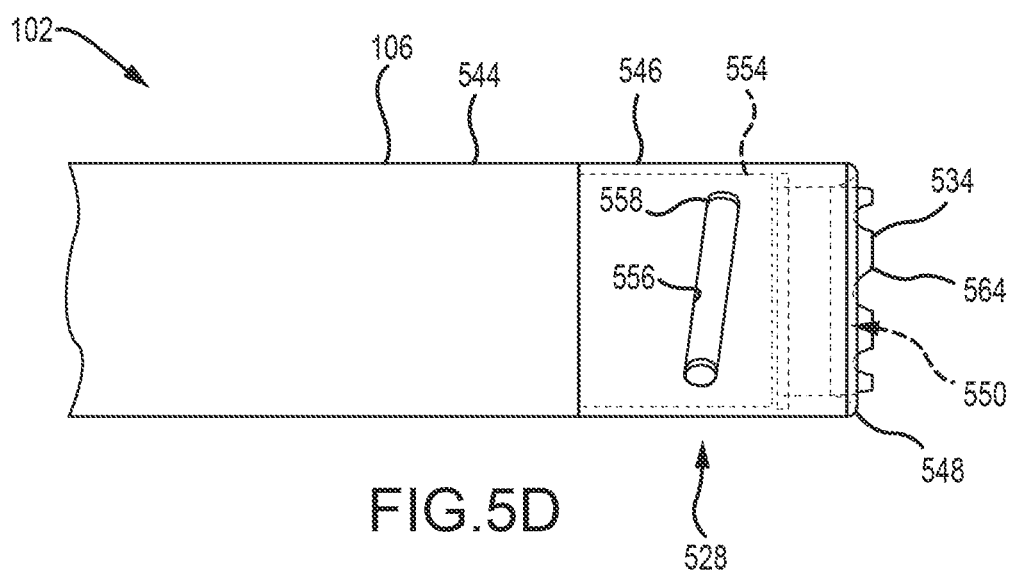
FIG. 5D is another detail view of the sheath assembly of the surgical device within line 5-5 of FIG. 3A; the surgical device is illustrated in a second extended configuration in which the cutting tip further protrudes from the outer shield.

Referring to FIGS. 3, 4A, and 4B, the housing 308 of the handle assembly 104 further carries a shield drive mechanism 318. The shield drive mechanism 318 may be actuated by the user of the surgical device 100 to reconfigure the device from a shielded configuration (that is, a configuration in which the cutting tip is disposed within the outer sheath assembly 106) to an extended configuration (that is, a configuration in which the cutting tip at least partially protrudes from the outer sheath assembly 106) and vice versa. In some embodiments and as illustrated in the figures, the shield drive mechanism 318 is carried near a distal end of the housing 308 of the handle assembly 104. The shield drive mechanism 318 may include a base 320 that fixedly couples to the housing 308 of the handle assembly 104 via, for example, fasteners (not shown) or the like. The base 320 may be formed of various appropriate materials, such as polymers and the like. The base 320 may rotatably couple to an actuatable component or "chuck" 322 via, for example, a bearing (not shown). The chuck 322 may be formed of various appropriate materials, such as polymers and the like. As described in further detail below, one or more components of the sheath assembly 102 may extend through a passageway 424 defined by the base 320 and the chuck 322.

The chuck 322 may fixedly couple to a proximal end of the outer sheath assembly 106 via, for example, one or more fasteners, adhesives, or the like. The chuck 322 may be rotated about a longitudinal axis 326 of the sheath assembly 102 to translate the outer sheath assembly 106 relative to the cutting tip and thereby reconfigure the device 100 from the shielded configuration to the extended configuration and vice versa. Referring briefly to FIGS. 5A-5D, rotation of the chuck 322 about the longitudinal axis 326 causes the device 100 to change configurations due to the presence of a shield cam and follower mechanism 528 defined at the distal end of the sheath assembly 102. The cam and follower mechanism 528 causes translation of the outer sheath assembly 106 relative to the cutting tip upon rotation of the chuck 322. Returning to FIGS. 3, 4A, and 4B, for example, when the surgical device 100 is in a first configuration (for example, the shielded configuration), the chuck 322 may be rotated in a first direction about the longitudinal axis (for example, a clockwise direction viewing the device 100 from the proximal end to the distal end) to reconfigure the device 100 to a second configuration (for example, the extended configuration). Conversely, when the surgical device 100 is in the second configuration, the chuck 322 may be rotated in a second direction about the longitudinal axis (for example, a counter-clockwise direction viewing the device 100 from the proximal end to the distal end) to reconfigure the device 100 to the first configuration. In some embodiments, the chuck 322 rotates about 90 degrees relative to the base 320 to reconfigure the device 100 from the first configuration to the second configuration and vice versa. Alternatively, the chuck 322 may rotate over various other angles relative to the base 320 to reconfigure the device 100 from the first configuration to the second configuration and vice versa.

In some embodiments, the shield drive mechanism 318 includes a detent mechanism 430 (see FIG. 4B) that maintains the chuck 322 in its rotational orientation relative to the base 320 in the shielded configuration and/or the extended configuration of the device 100 (that is, a "shielded rotational orientation" and/or an "extended rotational orientation"). A holding force provided by the detent mechanism 430 may be overcome to rotate the chuck 322 relative to the base 320 as described above. In some embodiments and as illustrated in the figures, the detent mechanism 430 may be formed by a component 432 of the base 320 that includes several flat outer surfaces and a spring-biased pin 433 that is carried by the chuck 322 and engages the flat surfaces of the component 432.

In some embodiments, the detent mechanism 430 may define one or more shielded configurations and one or more extended configurations for the surgical device 100. For example and as illustrated in the figures, the surgical device 100 may be configurable to a shielded configuration (see, for example, FIG. 5B; that is, a configuration in which the cutting tip 534 is disposed within the outer sheath assembly 106; this configuration is also referred to as a "flush" configuration because the cutting surface 564 is flush with the distal surface 548), a first extended configuration (see, for example, FIG. 5C; that is, a configuration in which the cutting tip 534 partially protrudes from the outer sheath assembly 106, for example, by 0.010 inches; this configuration is also referred to as a "partially extended" configuration), and a second extended configuration (see, for example, FIG. 5D; that is, a configuration in which the cutting tip 534 further protrudes from the outer sheath assembly 106, for example, by 0.020 inches; this configuration is also referred to as a "fully extended" configuration). In some embodiments, when the device 100 is in the first extended configuration, the chuck 322 rotates about 45 degrees relative to the base 320 in a first direction (for example, a clockwise direction viewing the device 100 from the proximal end to the distal end) to reconfigure the device 100 from the first extended configuration to the second extended configuration and vice versa. In some embodiments, when the device 100 is in the first extended configuration, the chuck 322 rotates about 45 degrees relative to the base 320 in a second direction (for example, a counter-clockwise direction viewing the device 100 from the proximal end to the distal end) to reconfigure the device 100 from the first extended configuration to the shielded configuration and vice versa. Alternatively, the chuck 322 may rotate over various other angles relative to the base 320 to reconfigure the device 100 from the first extended configuration to the second extended configuration and vice versa, and to reconfigure the device 100 from the first extended configuration to the shielded configuration and vice versa.

In some embodiments, the chuck 322 may include one or more indicators (for example, three indictors 436A, 436B, and 436C) that align with an indicator 438 on the base 320 in the shielded and/or extended configurations of the device 100. For example, the first indicator 436A may longitudinally align with the base indicator 438 in the shielded configuration, the second indicator 436B may longitudinally align with the base indicator 438 in the first extended configuration (the partially extended configuration), and the third indicator 436C may longitudinally align with the base indicator 438 in the second extended configuration (the fully extended configuration). In some embodiments, the indicators 436A, 436B, and 436C may be different colors. For example, the first indicator 436A may be green the second indicator 436B may be yellow, and the third indictor 436C may be red. The indicators 436 and 438 may be formed as various types and different combinations of symbols and/or shapes, such as circles or the like. Additionally, although FIGS. 4A and 4B illustrate three (3) indicators 436A, 436B and 436C, corresponding to the shielded configuration, the first extended configuration, and the fully extended configuration, the device 100, including the chuck 322, may have additional shielded, extended or other configurations. As such, the device 100 and the chuck 322 may have additionally corresponding indicators indicative of such configurations.

Referring again to FIGS. 5A-5D, the sheath assembly 102 may be generally flexible in order to accept, accommodate, and navigate the patient's vasculature system. The sheath assembly 102 generally includes the outer sheath assembly 106, an intermediate sheath assembly 540 carried within the outer sheath assembly 106, and an inner sheath assembly 542 carried within the intermediate sheath assembly 540.

The outer sheath assembly 106 includes an outer sheath 544. The outer sheath 544 may be formed of a polymer extrusion, braided reinforced polymer extrusion, coils, bi-coils, tri-coils, laser cut metal tubing and any combination of the above. In some embodiments, the outer sheath 544 includes a jacket, such as a flexible polymer jacket, that surrounds the above component(s). The outer sheath 544 may be a unitary structure that includes multiple portions. In some embodiments, the outer sheath 544 has an outer diameter of about 0.203 inches and an inner diameter of about 0.189 inches. In some embodiments, the outer sheath 544 has an outer diameter of about 0.250 inches and an inner diameter of about 0.230 inches. A proximal end of the outer sheath 544 may be fixedly coupled to the chuck 322. Alternatively, and as explained in further detail below, the proximal end of the outer sheath 544 may be rotatably fixed and translatably slidable relative to the chuck 322. A distal end of the outer sheath 544 couples to an outer shield or outer band 546 via, for example, a welded connection or the like.

The outer shield 546 is illustrated separately in FIGS. 6A and 6B. The outer shield 546 is a generally annular-shaped component that be formed of various appropriate components, such as biocompatible metals or the like. The outer shield 546 includes a distal surface 548 opposite the outer sheath 544. In some embodiments, the distal surface 548 is a curved, polished, and/or generally smooth surface that facilitates dilating tissue of the subject. The distal surface 548 defines a distal opening 550 that receives an implanted lead and, in some cases, a portion of the tissue surrounding the implanted lead. In addition, the cutting tip 534 extends at least partially through the distal opening 550 in extended configurations of the surgical device 100 (see, for example, FIGS. 5C and 5D). The distal opening 550 is in communication with an outer shield passageway 551 that extends from the distal surface 548 to a proximal end of the outer shield 546.

The intermediate sheath assembly 540 includes an intermediate sheath 552 that is carried within the outer sheath 544. The intermediate sheath 552 may be formed of a polymer extrusion, braided reinforced polymer extrusion, coils, bi-coils, tri-coils, laser cut metal tubing and any combination of the above. The intermediate sheath 552 may be a unitary structure that includes multiple portions. In some embodiments, the intermediate sheath 552 has an outer diameter of about 0.180 inches and an inner diameter of about 0.166 inches. In some embodiments, the intermediate sheath 552 has an outer diameter of about 0.219 inches and an inner diameter of about 0.205 inches. A proximal end of the intermediate sheath 552 may be fixedly coupled to the base 320 of the shield drive mechanism 318. Alternatively, the intermediate sheath 552 may extend through the passageway 424 of the base 320 and the proximal end of the intermediate sheath 552 may be fixedly coupled to the housing 308 of the handle assembly 104. A distal end of the intermediate sheath 552 couples to an intermediate tip 554 via, for example, a welded connection or the like.

The intermediate tip 554 is illustrated separately in FIGS. 7A and 7B. The intermediate tip 554 may be formed of various appropriate components, such as biocompatible metals or the like. The intermediate tip 554 is a generally annular-shaped component that is carried in the outer shield passageway 551. The intermediate tip 554 includes an intermediate tip passageway 555 that extends from a distal end to a proximal end of the intermediate tip 554.

Referring now to FIGS. 5A-5D, 6A-6B, and 7A-7B and as described briefly above, the outer shield 546 and the intermediate tip 554 together define a shield cam and follower mechanism 528. The cam and follower mechanism 528 causes translation of a least a portion of the outer sheath assembly 106 (for example, the distal portion) relative to the intermediate sheath assembly 540 and the cutting tip 534 upon actuation of the shield drive mechanism 318 and rotation of the outer sheath assembly 106 (for example, upon rotation of the chuck 322). In some embodiments, the cam and follower mechanism 528 includes a cam slot or channel 556 defined by the outer shield 546 and a follower or pin 558 carried by the intermediate tip 554. In some embodiments, the pin 558 is press-fittingly received in a through hole 559 defined by the intermediate tip 554. Alternatively, the cam slot 556 may be defined by the intermediate tip 554 and the follower 558 may be carried by the outer shield 546. In either case, the cam slot 556 slidably receives the follower 558. In addition, the cam slot 556 includes a profile that extends longitudinally and over at least a portion of the circumference of (that is, partially helically around) the outer shield 546 (or, alternatively, the intermediate tip 554). As a result, when the outer sheath 544 and the outer shield 546 rotate relative to the intermediate sheath assembly 540 (due to, for example, rotation of the chuck 322), the follower 558 slides in the cam slot 556, and the profile of the cam slot 556 controls longitudinal translation of the outer shield 546 relative to the intermediate tip 554 and the cutting tip 534. Stated another way, the profile of the cam slot 556 controls translation of the outer shield 546 from one or more first positions in which the cutting tip 534 is disposed within the outer shield 546 (that is, one or more of the shielded configurations of the device 100; see, for example, FIG. 5B) to one or more second positions in which the cutting tip 534 extends at least partially through the distal opening 550 (that is, one or more of the extended configurations of the device 100; see, for example, FIGS. 5C and 5D) and vice versa.

In some embodiments and as illustrated in the figures, the cam slot 556 includes a linear profile. Alternatively, the cam slot 556 may include a non-linear profile or a combination of individual and/or multiple linear and non-linear profiles.

In some embodiments, translation and rotation of the outer shield 546 relative to the intermediate sheath assembly 540 (due to rotation of the chuck 322 and the outer sheath 544) causes a relatively small amount of longitudinal compression and extension of the outer sheath 544 between the chuck 322 and the outer shield 546 (for example, about 0.020 inches of longitudinal compression and extension). Stated another way, the proximal end of the outer sheath 544 is fixedly coupled to the chuck 322, and the proximal end of the outer sheath 544 does not translate as the outer shield 546 translates and rotates relative to the intermediate sheath assembly 540. Alternatively and in some embodiments, translation and rotation of the outer shield 546 relative to the intermediate sheath assembly 540 (due to rotation of the chuck 322 and the outer sheath 544) causes translation and/or rotation of the proximal end of the outer sheath 544 relative to the chuck 322. Stated another way, the proximal end of the outer sheath 544 is translatably and/or rotationally coupled to the chuck 322.

Referring again to FIGS. 5A-5D, the inner sheath assembly 542 includes an inner sheath 560 that is rotatably carried by the intermediate sheath 552. The inner sheath 560 may be formed of a polymer extrusion, braided reinforced polymer extrusion, coils, bi-coils, tri-coils, laser cut metal tubing and any combination of the above. The inner sheath 560 may be a unitary structure that includes multiple portions. In addition to being flexible, the inner sheath 560 may also have a high degree of rotational stiffness in order to receive the torque transferred from the cutting tip drive mechanism 314 and transfer sufficient torque to the cutting tip 534. In some embodiments, the inner sheath 560 has an outer diameter of about 0.156 inches and an inner diameter of about 0.136 inches. In some embodiments, the inner sheath 560 has an outer diameter of about 0.196 inches and an inner diameter of about 0.177 inches. A proximal end of the inner sheath 560 may be rotatably fixed and translatably slidable relative to the cutting tip drive mechanism 314 via, for example, a key assembly 362 (see FIG. 3A), such as an assembly including any of the inner keys and outer keys described and/or illustrated in U.S. Provisional Patent Application No. 62/058,790. A distal end of the inner sheath 560 couples to the cutting tip 534 via, for example, a welded connection or the like.

The cutting tip 534 is illustrated separately in FIGS. 8A-8D. The cutting tip 534 may be formed of various appropriate components, such as biocompatible metals or the like. The cutting tip 534 is a generally annular shaped-component that is carried in the intermediate tip passageway 555. A distal end of the cutting tip 534 includes a cutting surface 564 that is adapted to cut tissue of the subject when the cutting tip 534 rotates relative to the intermediate tip 554

(for example, upon actuation of the cutting tip drive mechanism 314 and rotation of the inner sheath 560 relative to the intermediate sheath 552). In some embodiments, the cutting surface 564 is adapted to cut tissue of the subject in both the shielded configuration(s) and the extended configuration(s) of the surgical device 100.

Figure 8A:
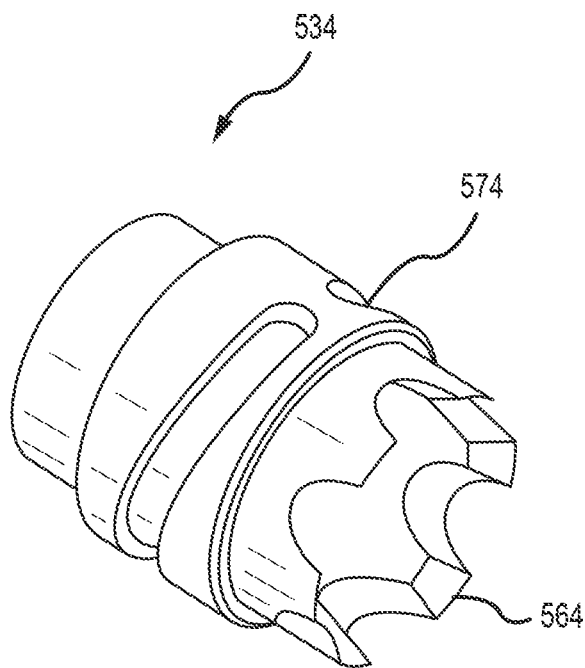
FIG. 8A is a perspective view of an embodiment of a cutting tip of the surgical device of FIG. 1.
Figure 8B:
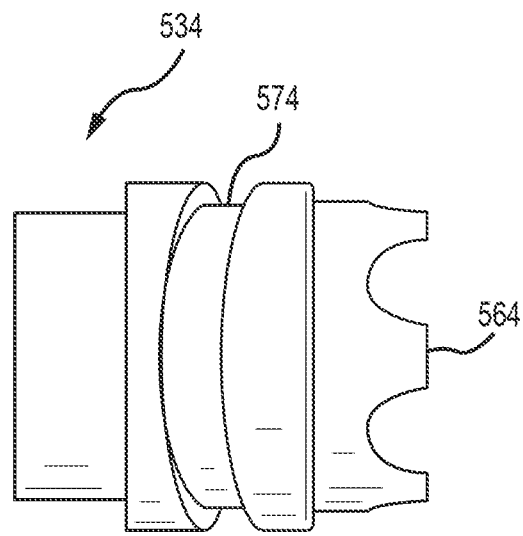
FIG. 8B is a side view of the cutting tip illustrated in FIG. 8A.
Figure 8C:
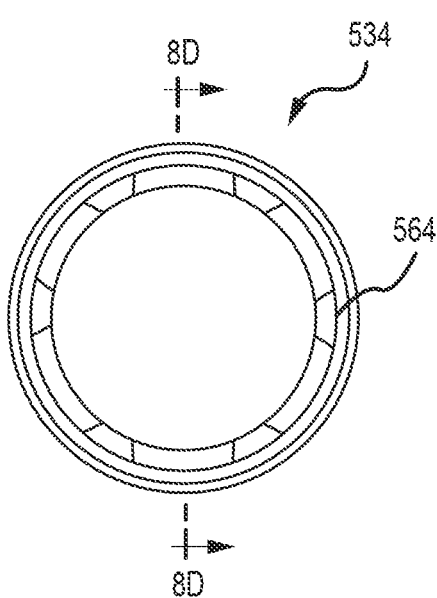
FIG. 8C is an end view of the cutting tip illustrated in FIG. 8A.
Figure 8D:
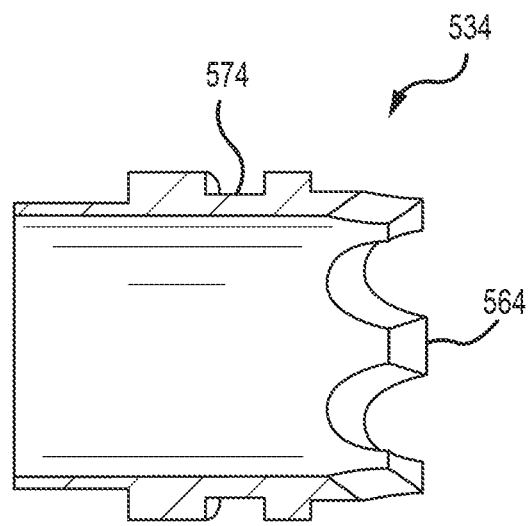
FIG. 8D is a cross-sectional view of the cutting tip illustrated in FIG. 8A taken along line 8D-8D in FIG. 8C.
Figure 9A:
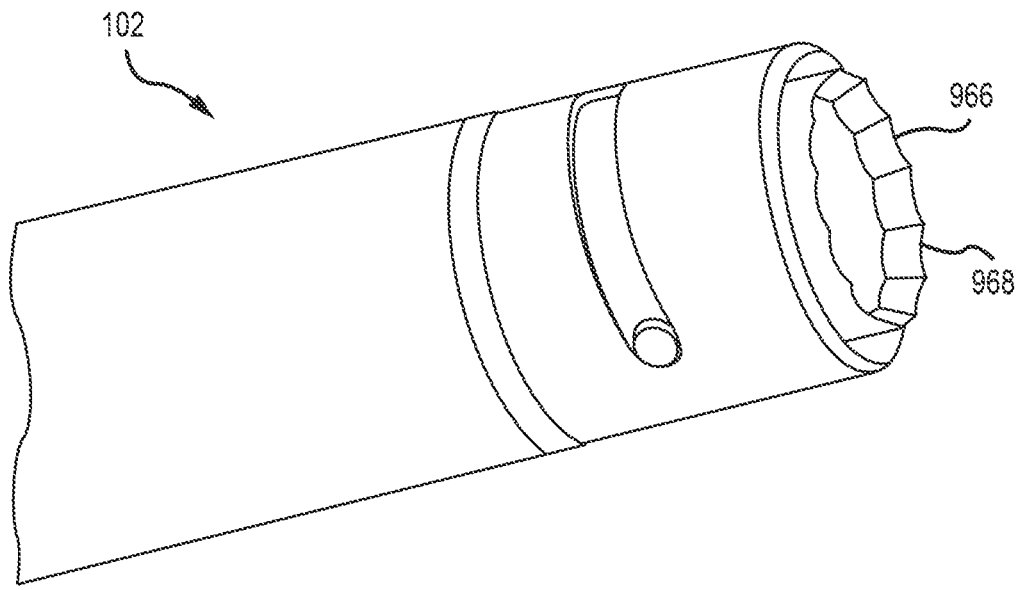
FIG. 9A is a detail view of the surgical device of FIG. 1 including another embodiment of a cutting tip.
Figure 9B:
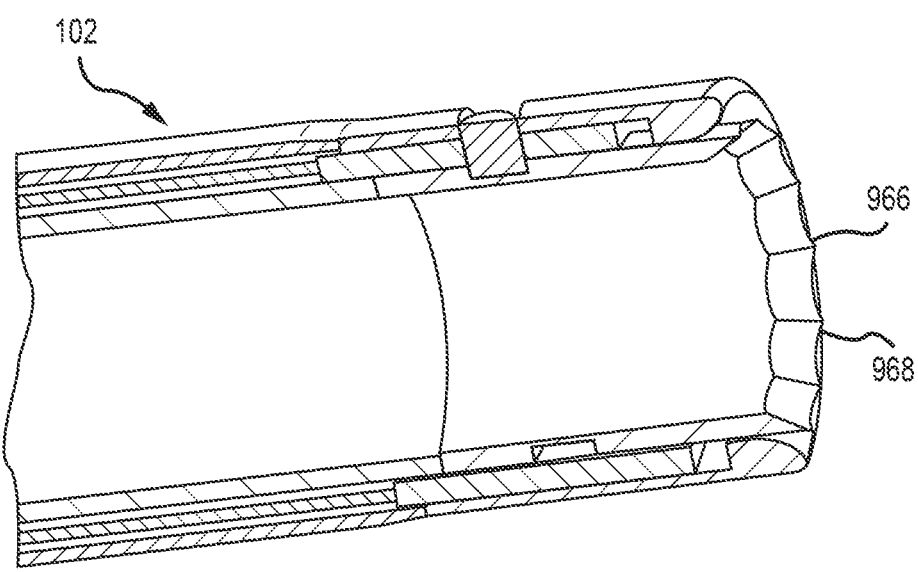
FIG. 9B is a longitudinal sectional view of the surgical device of FIG. 9A.

In some embodiments and as shown in FIGS. 8A-8D, the cutting surface 564 may be formed as a "crown" serration (that is, a surface that includes a plurality of notches and adjacent un-notched areas). Alternatively and as shown in FIGS. 9A and 9B, the sheath assembly 102 may include a cutting tip 966 that has a cutting surface 968 formed as another type of serration. Specifically, the cutting surface 968 may be formed as a serration that includes a plurality of notches but lacks adjacent un-notched areas. As another alternative, the cutting surface of a cutting tip may lack a serration. The remainder of this description only refers to the cutting tip 534 for brevity, although it is to be understood that any description of the cutting tip 534 also applies to the cutting tip 966.

Figure 10:
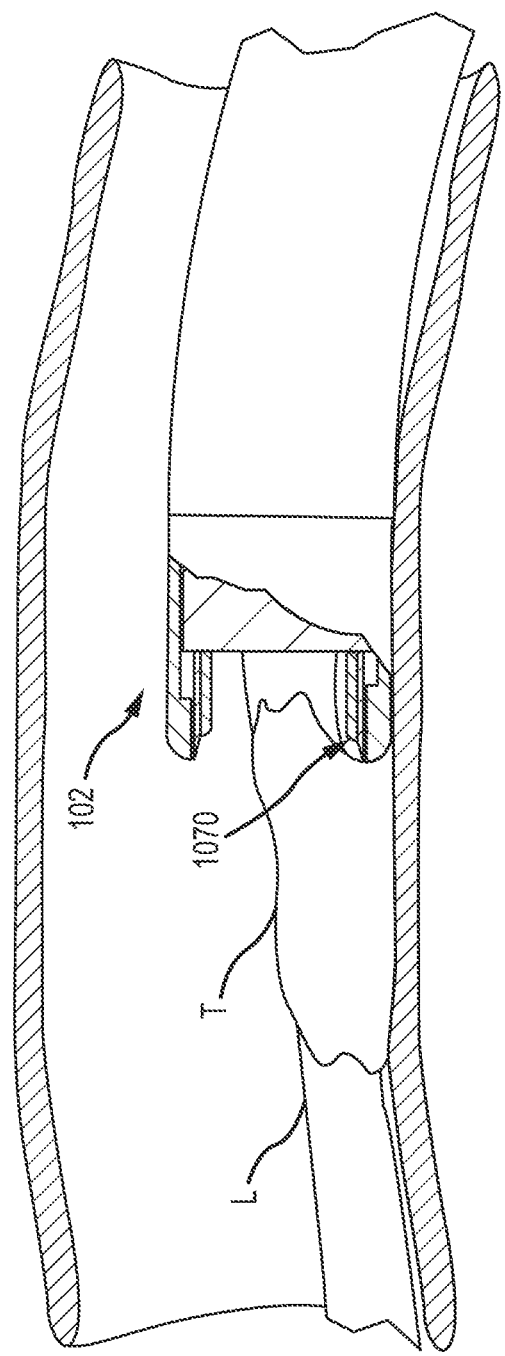
FIG. 10 is a partial longitudinal sectional view of the surgical device of FIG. 1 including another embodiment of a cutting tip.

As yet another alternative, the cutting surface of a cutting tip may include various other profiles, such as any of those described and/or illustrated in U.S. patent application Ser. No. 13/834,405, which is hereby incorporated by reference in its entirety for all it teaches and for all purposes. In addition and referring to FIG. 10, any of the cutting tips described herein may include an inner surface 1070. The inner surface 1070 may be disposed radially inwardly and proximally relative to the cutting surface 564. The inner surface 1070 may be a curved, polished, and/or generally smooth surface that facilitates guiding cut tissue T and/or an implanted lead L into the sheath assembly 102.

Referring again to FIGS. 5A-5D and 8A-8D, in some embodiments, the cutting tip 534 simply rotates relative to the intermediate tip 554 and the outer shield 546 upon actuation of the cutting tip drive mechanism 314 (that is, the cutting tip 534 does not translate longitudinally relative to the intermediate tip 554 and the outer shield 546 upon actuation of the cutting tip drive mechanism 314). In some embodiments, the cutting tip 534 rotates and translates longitudinally relative to the intermediate tip 554 and the outer shield 546 upon actuation of the cutting tip drive mechanism 314. To facilitate this translation, in some embodiments the surgical device 100 includes a cutting tip cam and follower mechanism 572 defined at the distal end of the sheath assembly 102. That is, the cam and follower mechanism 572 causes translation of the cutting tip 534 relative to the intermediate tip 554 and the outer shield 546 upon actuation of the cutting tip drive mechanism 314 and rotation of the cutting tip 534 (for example, by proximally and distally translating the trigger 310). In some embodiments, the cam and follower mechanism 572 includes a cam slot or channel 574 defined by the cutting tip 534 and the follower or pin 558 carried by the intermediate tip 554. Alternatively, the cam slot 574 may be defined by the intermediate tip 554 and the follower 558 may be carried by the cutting tip 534. As another alternative, the cutting tip cam and follower mechanism 572 may include a different follower or pin (not shown) than the shield cam and follower mechanism 528. In any case, the cam slot 574 slidably receives the follower 558. In addition, the cam slot 574 includes a profile that extends longitudinally and over at least a portion of the circumference of the cutting tip 534 (or, alternatively, the intermediate tip 554). As a result, when the inner sheath 560 and the cutting tip 534 rotate relative to the intermediate sheath assembly 540 (due to, for example, translation of the trigger 310 and actuation of the cutting tip drive mechanism 314), the follower 558 slides in the cam slot 574, and the profile of the cam slot 574 controls longitudinal translation of the cutting tip 534 relative to the intermediate tip 554 and the outer shield 546.

The profile of the cam slot 574 may take a variety of forms, including any of those described and/or illustrated in U.S. Provisional Patent Application No. 62/058,790 or U.S. patent application Ser. No. 13/834,405. For example, the cam slot 574 may have a substantially linear profile, a substantially sinusoidal profile, or a combination of individual and/or multiple linear and non-linear profiles. Additionally, the cam slot 574 may have an open and continuous configuration, thereby allowing the cutting tip 534 to continuously rotate. Alternatively, the cam slot 574 may have a closed and discontinuous configuration such that when the cutting tip 534 reaches a fully rotated orientation, the trigger 310 must be released or reversed so that the cutting tip 534 returns to an initial orientation before being re-actuated. For instance, the cam slot 574 in FIG. 8A is discontinuous because the cam slot 574 does not travel around the entire circumference of the exterior of the cutting tip 534. Furthermore, the cam slot 574 may be a partial lobe cam (which includes a cam slot surrounding less than 360 degrees of the circumference of the exterior surface of the cutting tip 534), a single lobe cam (which includes a cam slot surrounding 360 degrees of the circumference of the exterior surface of the cutting tip 534), a double lobe cam (which includes a cam slot surrounding 720 degrees of the circumference of the exterior surface of the cutting tip 534) and/or other multiple lobe cams.

As described above, in the shielded configuration(s) of the device 100, the cutting surface 564 of the cutting tip 534 is disposed within the outer shield 546 when the cutting tip drive mechanism 314 is not actuated. In some embodiments, the cam slot 574 includes a profile such that, in one or more shielded configurations of the device 100, the cutting surface 564 remains disposed within the outer shield 546 during actuation of the cutting tip drive mechanism 314. In some embodiments, such a device 100 reduces the risk of damaging the wall of the vessel because the cutting surface 564 remains shielded during actuation of the cutting tip drive mechanism 314 because the cutting surface 564 remains proximal of the most distal end of the outer shield 546, even during rotation and extension of the cutting tip 534 within the outer shield 546. In some embodiments, the cam slot 574 includes a profile such that, in one or more shielded configurations of the device 100, the cutting surface 564 extends through the distal opening 550 of the outer shield 546 and is at least partially disposed outside of the outer shield 546 during a portion of actuation of the cutting tip drive mechanism 314.

As described above, in the extended configuration(s) of the device 100, the cutting surface 564 of the cutting tip 534 is at least partially disposed outside of the outer shield 546 when the cutting tip drive mechanism 314 is not actuated. In some embodiments, the cam slot 574 includes a profile such that, in one or more extended configurations of the device 100, the cutting surface 564 remains at least partially disposed outside of the outer shield 546 during actuation of the cutting tip drive mechanism 314. In some embodiments, the cam slot 574 includes a profile such that, in one or more extended configurations of the device 100, the cutting surface 564 retracts through the distal opening 550 of the outer shield 546 and is disposed within the outer shield 546 during a portion of actuation of the cutting tip drive mechanism 314.

In some embodiments and as illustrated in FIGS. 1-10, the surgical device 100 includes a cutting tip 534 that has a "flat" cutting surface 564. That is, the cutting surface 564 is perpendicular relative to the longitudinal axis 326 of the sheath assembly 102. In some embodiments, the distal surface 548 of the outer shield 546 is also perpendicular relative to the longitudinal axis 326 of the sheath assembly 102.

Referring now to FIGS. 11A-11E, in some embodiments the surgical device 100 includes a sheath assembly 1176 that has a "beveled", "diagonal", or "offset" distal end. That is, the sheath assembly 1176 includes a cutting tip 1178 that has a "beveled", "diagonal", or "offset" cutting surface 1180 and/or an outer shield 1182 that has a "beveled", "diagonal", or "offset" distal opening 1184. That is, in some embodiments the cutting surface 1180 of the cutting tip 1178 is disposed at an acute angle $\alpha$ relative to the longitudinal axis 326. In some embodiments, the distal opening 1184 of the outer shield 1182 is disposed at an acute angle $\beta$ relative to the longitudinal axis 326. In some embodiments, angle $\alpha$ and angle $\beta$ are equal. In some embodiments, angle $\alpha$ and angle $\beta$ are not equal.

The cutting surface 1180 may have various types of serrations, such as those described above, or it may lack serrations.

Figure 11A:
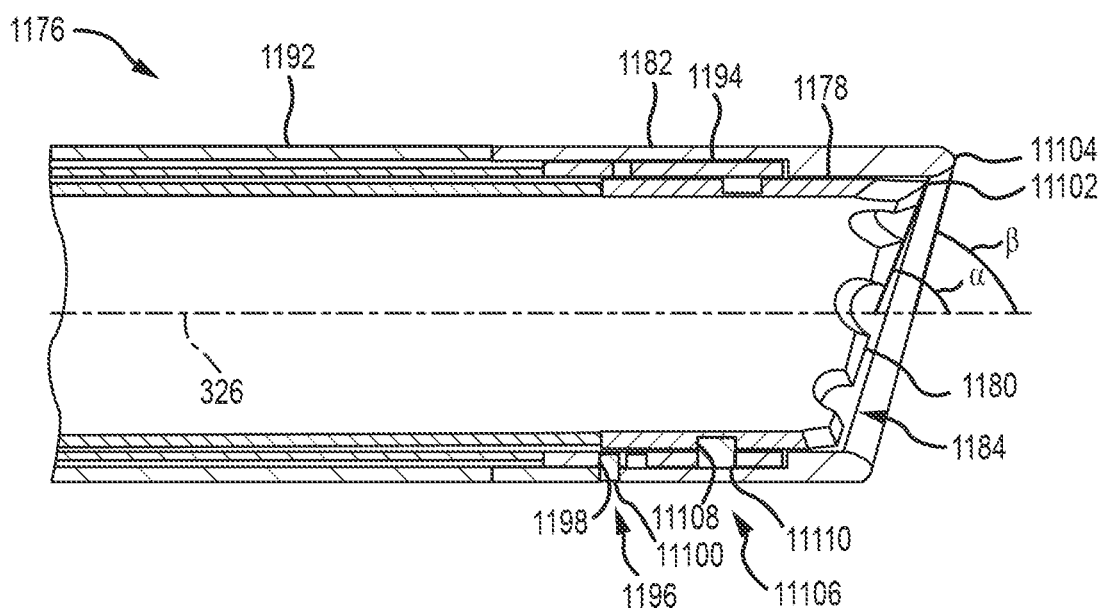
FIG. 11A is a detail, longitudinal sectional view of a sheath assembly of an embodiment of a surgical device.
Figure 11B:
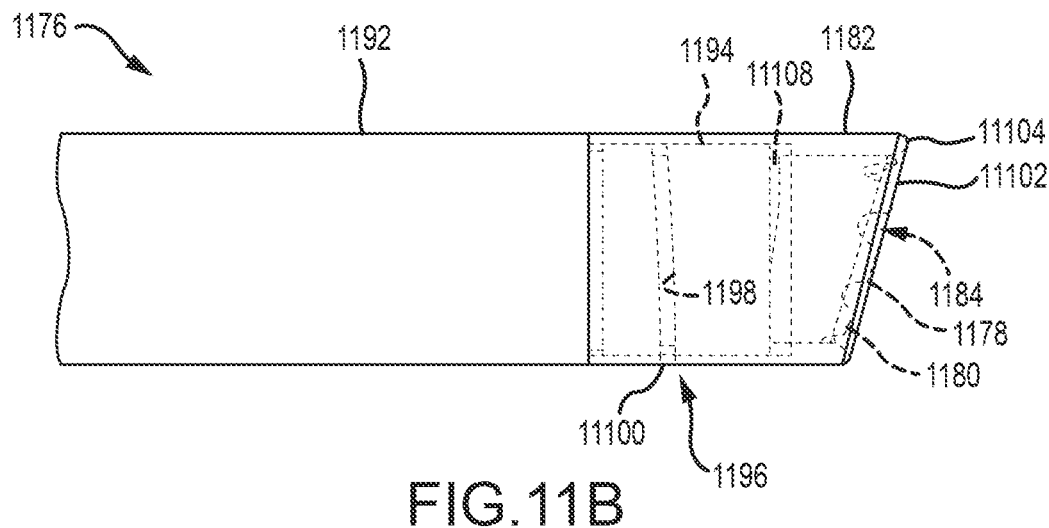
FIG. 11B is a detail view of the sheath assembly of FIG. 11A; the sheath assembly is illustrated in a shielded configuration in which a cutting tip is disposed within an outer shield, and an apex of the cutting tip is illustrated as being rotated out of angular alignment with an apex of the outer shield.
Figure 11C:
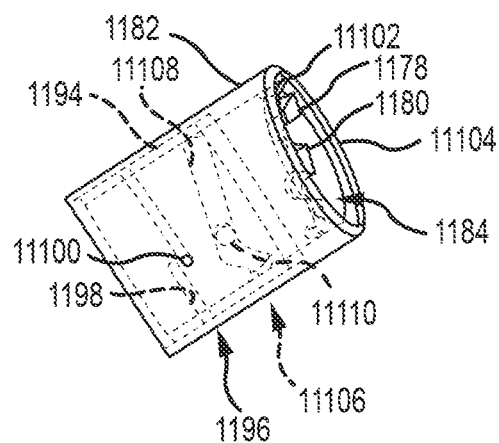
FIG. 11C is a detail view of the outer shield, an intermediate tip, and the cutting tip of the sheath assembly of FIG. 11A; the components are illustrated in the shielded configuration in which the cutting tip is disposed within the outer shield, and the apex of the cutting tip is illustrated as being rotated out of angular alignment with the apex of the outer shield.
Figure 11D:
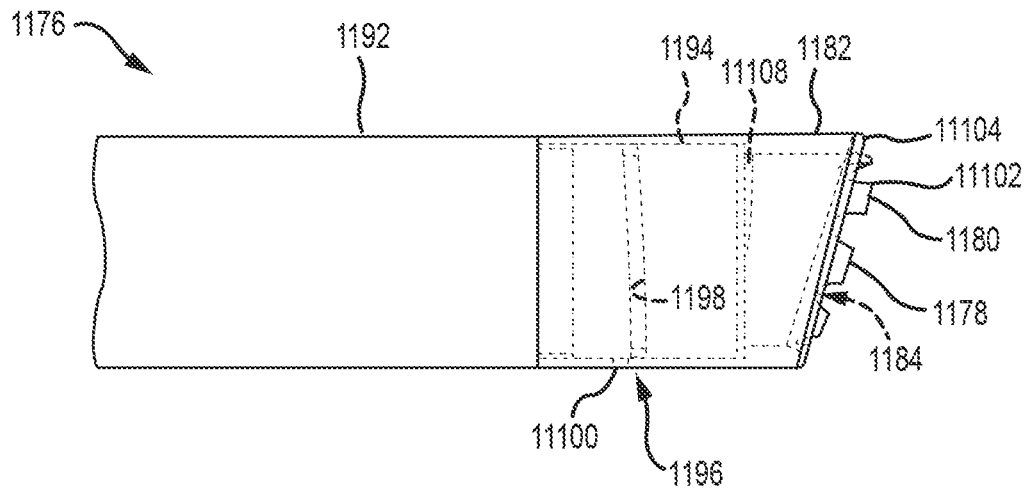
FIG. 11D is another detail view of the sheath assembly of FIG. 11A; the sheath assembly is illustrated in an extended configuration in which the cutting tip partially protrudes from the outer shield, and the apex of the cutting tip is illustrated as being rotated out of angular alignment with the apex of the outer shield.
Figure 11E:
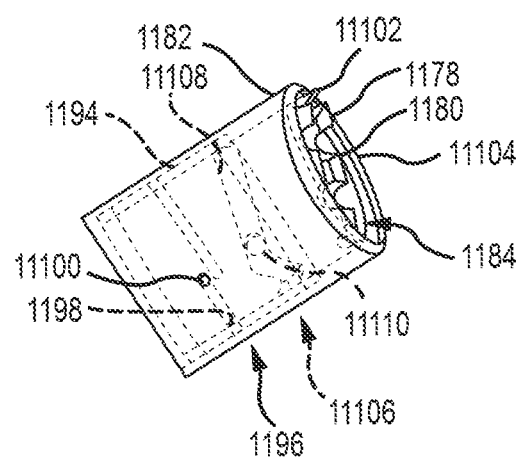
FIG. 11E is a detail view of the outer shield, the intermediate tip, and the cutting tip of the sheath assembly of FIG. 11A; the components are illustrated in an extended configuration in which the cutting tip partially protrudes from the outer shield, and the apex of the cutting tip is illustrated as being rotated out of angular alignment with the apex of the outer shield.

Referring specifically to FIGS. 11B and 11C, the cutting tip 1178 may rotate to cut, separate, and/or dilate tissue in one or more shielded configurations of the sheath assembly 1176 in which the cutting tip 1178 is disposed within the outer shield 1182. Referring specifically to FIGS. 11D and 11E, the cutting tip 1178 may also rotate to cut, separate, and/or dilate tissue in one or more extended configurations of the sheath assembly 1176 in which the cutting tip 1178 at least partially protrudes from the outer shield 1182.

Figure 12A:
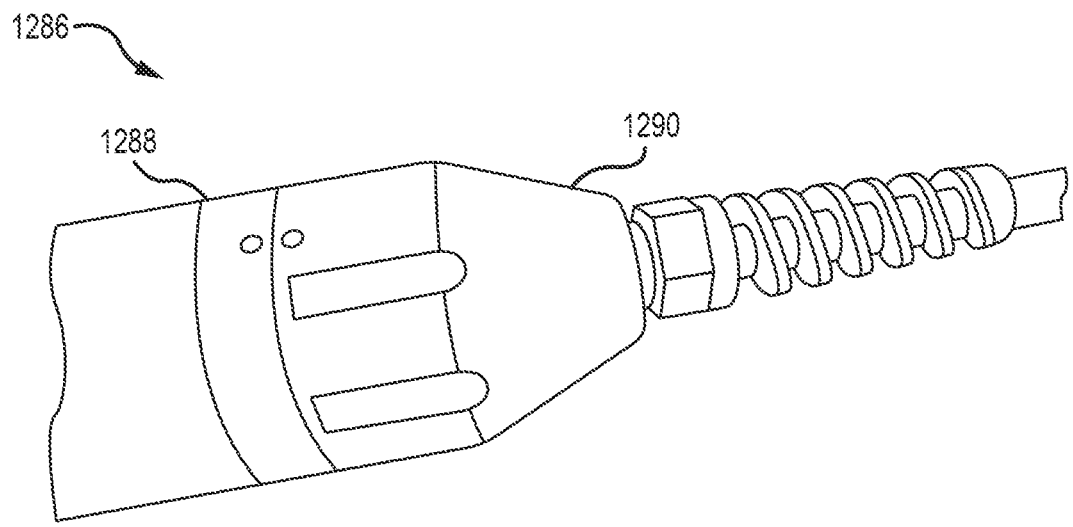
FIG. 12A is a perspective view of a shield drive mechanism associated with the sheath assembly of FIGS. 11A-11E.
Figure 12B:
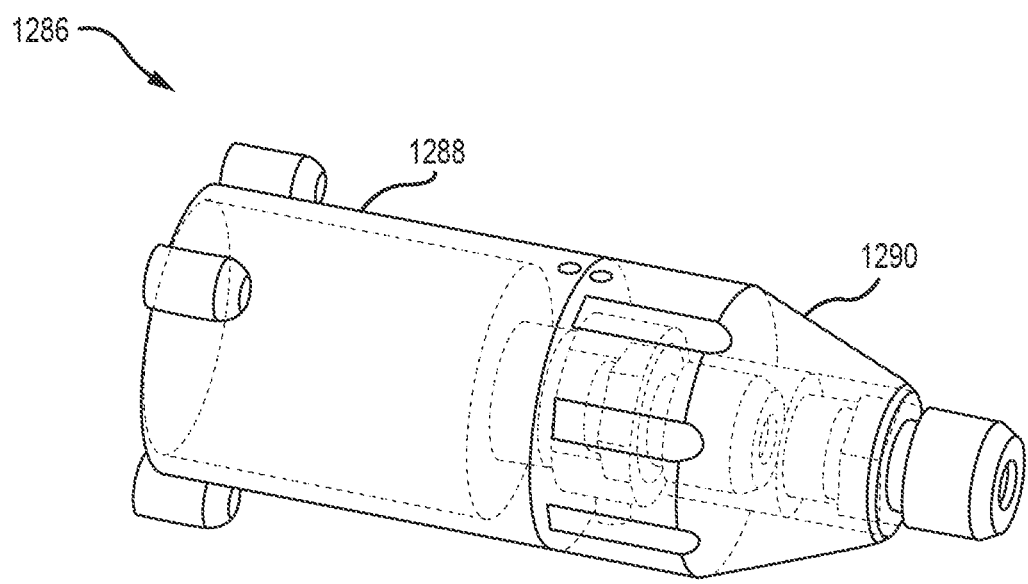
FIG. 12B is another perspective view of the shield drive mechanism of FIG. 12A.

The sheath assembly 1176 is selectively reconfigurable to move the cutting tip 1178 from the shielded configuration(s) to the extended configuration(s) and vice versa. Referring to FIGS. 12A and 12B, the device includes a shield drive mechanism 1286 that may be actuated by the user to reconfigure the sheath assembly 1176 from a shielded configuration to an extended configuration and vice versa. In some embodiments, the shield drive mechanism 1286 is carried near a distal end of the handle assembly (not shown). The shield drive mechanism 1286 may include a base 1288 that fixedly couples to the handle assembly. The base 1288 may rotatably couple to an actuatable component or "chuck" 1290.

Referring now to FIGS. 11A-11E and 12A-12B, the chuck 1290 couples to the outer shield 1182 via an outer sheath 1192. As such, rotation of the chuck 1290 about the longitudinal axis 326 causes rotation of the outer shield 1185 relative to the cutting tip 1178 and an intermediate tip 1194. As the outer shield 1185 rotates, the outer shield 1185 translates longitudinally relative to the cutting tip 1178 and the intermediate tip 1194 due to the presence of a shield cam and follower mechanism 1196.

In some embodiments, the cam and follower mechanism 1196 includes a cam slot or channel 1198 defined by the intermediate tip 1194 and a follower or pin 11100 carried by the outer shield 1182. Alternatively, the cam slot 1198 may be defined by the outer shield 1182 and the follower 11100 may be carried by the intermediate tip 1194. In either case, the cam slot 1198 slidably receives the follower 11100. In addition, the cam slot 1198 includes a profile that extends longitudinally and over at least a portion of the circumference of (that is, partially helically around) the intermediate tip 1194 (or, alternatively, outer shield 1182). As such, rotation of the outer shield 1182 relative to the intermediate tip 1194 (due to, for example, rotation of the chuck 1290) causes the outer shield 1182 to translate from one or more first positions in which the cutting tip 1178 is disposed within the outer shield 1182 (that is, one or more of the shielded configurations of the sheath assembly 1176; see, for example, FIGS. 11B and 11C) to one or more second positions in which the cutting tip 1178 extends at least partially through the distal opening 1184 (that is, one or more of the extended configurations of the sheath assembly 1176; see, for example, FIGS. 11D and 11E) and vice versa.

In some embodiments and as illustrated in the figures, the cam slot 1198 includes a linear profile. Alternatively, the cam slot 1198 may include a non-linear profile or a combination of individual and/or multiple linear and non-linear profiles. In some embodiments, the cam slot 1198 extends for 360 degrees about the circumference of the intermediate tip 1194 (or, alternatively, outer shield 1182) and the chuck 1290 rotates 360 degrees to reconfigure the sheath assembly 1176 from one of the shielded configurations to one of the extended configurations and vice versa. This facilitates angular alignment of an apex 11102 of the cutting surface 1180 with an apex 11104 of the outer shield 1182 in both the shielded configuration and the extended configuration.

In some embodiments, the cutting tip 1178 simply rotates relative to the intermediate tip 1194 and the outer shield 1182 upon actuation of the cutting tip drive mechanism (not shown in FIGS. 11A-12B; that is, the cutting tip 1178 does not translate longitudinally relative to the intermediate tip 1194 and the outer shield 1182 upon actuation of the cutting tip drive mechanism). In some embodiments, the cutting tip 1178 rotates and translates longitudinally relative to the intermediate tip 1194 and the outer shield 1182 upon actuation of the cutting tip drive mechanism. To facilitate this translation, in some embodiments the sheath assembly 1176 includes a cutting tip cam and follower mechanism 11106 defined at the distal end of the sheath assembly 1176. That is, the cam and follower mechanism 11106 causes translation of the cutting tip 1178 relative to the intermediate tip 1194 and the outer shield 1182 upon actuation of the cutting tip drive mechanism and rotation of the cutting tip 1178. In some embodiments, the cam and follower mechanism 11106 includes a cam slot or channel 11108 defined by the cutting tip 1178 and the follower or pin 11110 carried by the intermediate tip 1194. Alternatively, the cam slot 11108 may be defined by the intermediate tip 1194 and the follower 11110 may be carried by the cutting tip 1178. In either case, the cam slot 11108 slidably receives the follower 11110. In addition, the cam slot 11108 includes a profile that extends longitudinally and over at least a portion of the circumference of the cutting tip 1178 (or, alternatively, the intermediate tip 1194). As a result, when the cutting tip 1178 rotates relative to the intermediate tip 1194 (due to, for example, actuation of the cutting tip drive mechanism), the follower 11110 slides in the cam slot 11108, and the profile of the cam slot 11108 controls longitudinal translation of the cutting tip 1178 relative to the intermediate tip 1194 and the outer shield 1182. The profile of the cam slot 11108 may take a variety of forms, including any of those described above.

In the shielded configuration(s) of the sheath assembly 1176, the cutting surface 1180 of the cutting tip 1178 is disposed within the outer shield 1182 when the cutting tip drive mechanism is not actuated. In some embodiments, the cam slot 1198 includes a profile such that, in one or more shielded configurations of the sheath assembly 1176, the cutting surface 1180 remains disposed within the outer shield 1182 during actuation of the cutting tip drive mechanism. For example, in one or more shielded configurations the apex 11102 of the cutting tip 1178 may remain within the outer shield 1182 during a portion of actuation of the cutting tip drive mechanism. In some embodiments, the cam slot 1198 includes a profile such that, in one or more shielded configurations of the sheath assembly 1176, the cutting surface 1180 extends through the distal opening 1184 of the outer shield 1182 and is at least partially disposed outside of the outer shield 1182 during a portion of actuation of the cutting tip drive mechanism. For example, in one or more shielded configurations the apex 11102 of the cutting tip 1178 may be disposed outside of the outer shield 1182 during a portion of actuation of the cutting tip drive mechanism.

In the extended configuration(s) of the sheath assembly 1176, the cutting surface 1180 of the cutting tip 1178 is at least partially disposed outside of the outer shield 1182 when the cutting tip drive mechanism is not actuated. For example, the apex 11102 of the cutting tip 1178 may extend 0.020 inches distally past the outer shield 1182 when the cutting tip drive mechanism is not actuated. In some embodiments, the cam slot 1198 includes a profile such that, in one or more extended configurations of the sheath assembly 1176, the cutting surface 1180 remains at least partially disposed outside of the outer shield 1182 during actuation of the cutting tip drive mechanism. For example, in one or more extended configurations the apex 11102 of the cutting tip 1178 may remain disposed outside of the outer shield 1182 during a portion of actuation of the cutting tip drive mechanism. In some embodiments, the cam slot 1198 includes a profile such that, in one or more extended configurations of the sheath assembly 1176, the cutting surface 1180 retracts through the distal opening 1184 of the outer shield 1182 and is disposed within the outer shield 1182 during a portion of actuation of the cutting tip drive mechanism. For example, in one or more extended configurations the apex 11102 of the cutting tip 1178 may retract into the outer shield 1182 during a portion of actuation of the cutting tip drive mechanism.

Figure 13:
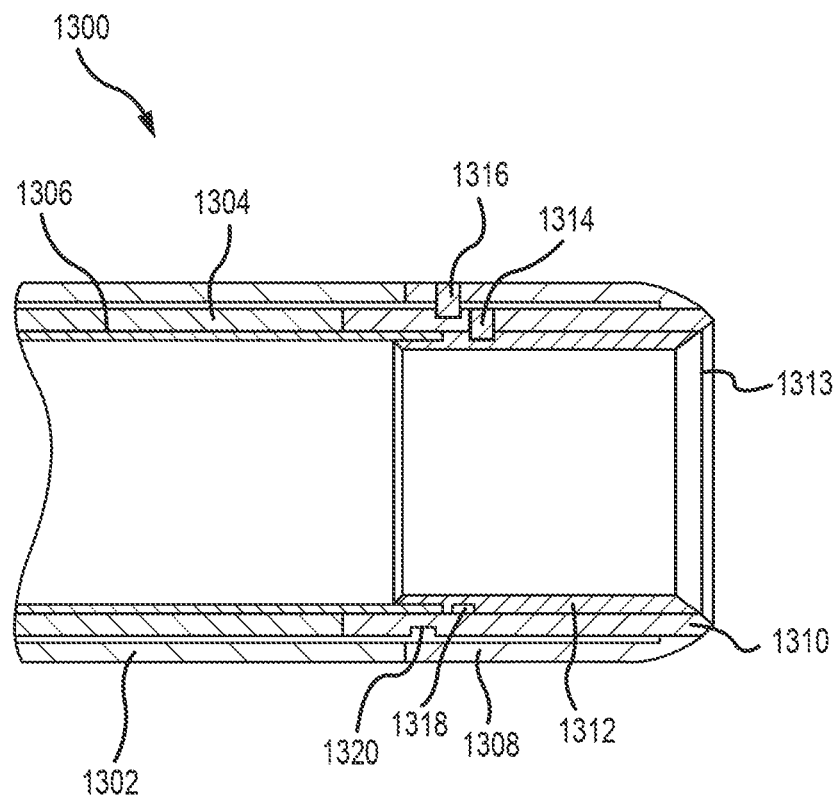
FIG. 13 is a detail, longitudinal sectional view of a sheath assembly of an embodiment of a surgical device.

Referring to FIG. 13, in some embodiments the surgical device 100 includes the sheath assembly 1300. This figure illustrates a flexible stationary outer sheath 1302, a flexible extendable intermediate sheath 1304, and a flexible extendable inner sheath 1306. Coupled to the outer sheath 1302 is a rotatable outer cam member 1308. Coupled to the intermediate sheath 1304 is a rotatable intermediate cam member 1310. Coupled to the inner sheath 1306 is a rotatable inner cam member 1312. The inner cam member 1312 includes a cutting surface 1313. The inner cam member 1312 is connected to the intermediate cam member 1310 by a pin 1314. The intermediate cam member 1310 is connected to the outer cam member by a pin 1316. As the inner sheath 1306 extends distally, the inner cam member 1312 rotates and travels according to the profile of a cam slot 1318 in which the pin 1314 sits. Similarly, as the intermediate sheath 1304 extends distally, the intermediate cam member rotates and travels according to the profile of a cam slot 1320 in which the pin 1316 sits.

Figure 14:
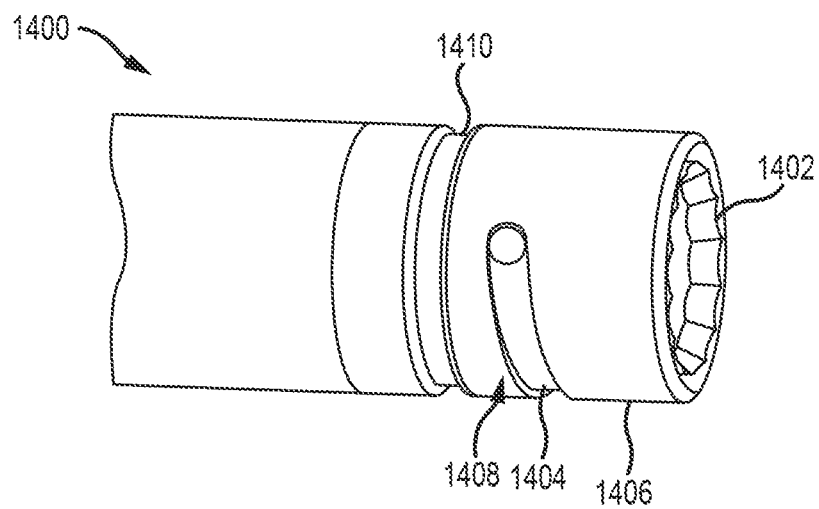
FIG. 14 is a detail view of a sheath assembly of an embodiment of a surgical device.

Referring to FIG. 14, in some embodiments the surgical device 100 includes the sheath assembly 1400. The sheath assembly 1400 may be similar to the sheath assemblies described above. Generally, sheath assembly 1400 includes a cutting tip 1402 that is received in an intermediate tip 1404. The cutting tip 1402 may be coupled to the intermediate tip 1404 via a cutting tip cam and follower mechanism (not shown in FIG. 14). The intermediate tip 1404 is received in an outer shield 1406. The outer shield 1406 may be coupled to the intermediate tip 1404 via a shield cam and follower mechanism 1408. The shield cam and follower mechanism 1408 facilitates moving the outer shield 1406 from one or more shielded configurations (see, for example, FIG. 14) to one or more extended configurations (not shown) and vice versa. In the shielded configurations, the cutting tip 1402 is disposed within the outer shield 1406. In the extended configurations, the cutting tip 1402 at least partially protrudes from the outer shield 1406. The outer shield 1406 may be moved from the shielded configuration to the extended configuration and vice versa by rotating the outer shield 1406 relative to the intermediate tip 1404. Stated another way, the shield cam and follower mechanism 1408 facilitates translation of the outer shield 1406 relative to the intermediate tip 1404 upon rotation of the outer shield 1406 relative to the intermediate tip 1404. In some embodiments, the sheath assembly 1400 may include one or more indicators that are exposed or visible when the outer shield 1406 is in a shielded configuration and/or an extended configuration. For example and as illustrated in FIG. 14, the intermediate tip 1404 may carry a colored band 1410 (for example, a green band) that is exposed in a shielded configuration. During use, the user may remove the distal end of the sheath assembly 1400 from the patient to move the outer shield 1406 from the shielded configuration to the extended configuration relative to the intermediate tip 1404 and vice versa.

The devices, structures, and components described herein may be combined or substituted with any of the devices, structures, and components described in U.S. patent application Ser. No. 14/577,976, entitled SURGICAL INSTRUMENT including an inwardly deflecting cutting tip FOR REMOVING AN IMPLANTED OBJECT, filed on Dec. 19, 2014, and/or U.S. application Ser. No. 15/249,206, filed Aug. 26, 2016, entitled MEDICAL DEVICE FOR REMOVING AN IMPLANTED OBJECT USING LASER CUT HYPOTUBES, which are hereby incorporated by reference in their entireties for all they teach and for all purposes. [Ryan, please begin your review here.]

Figure 15:
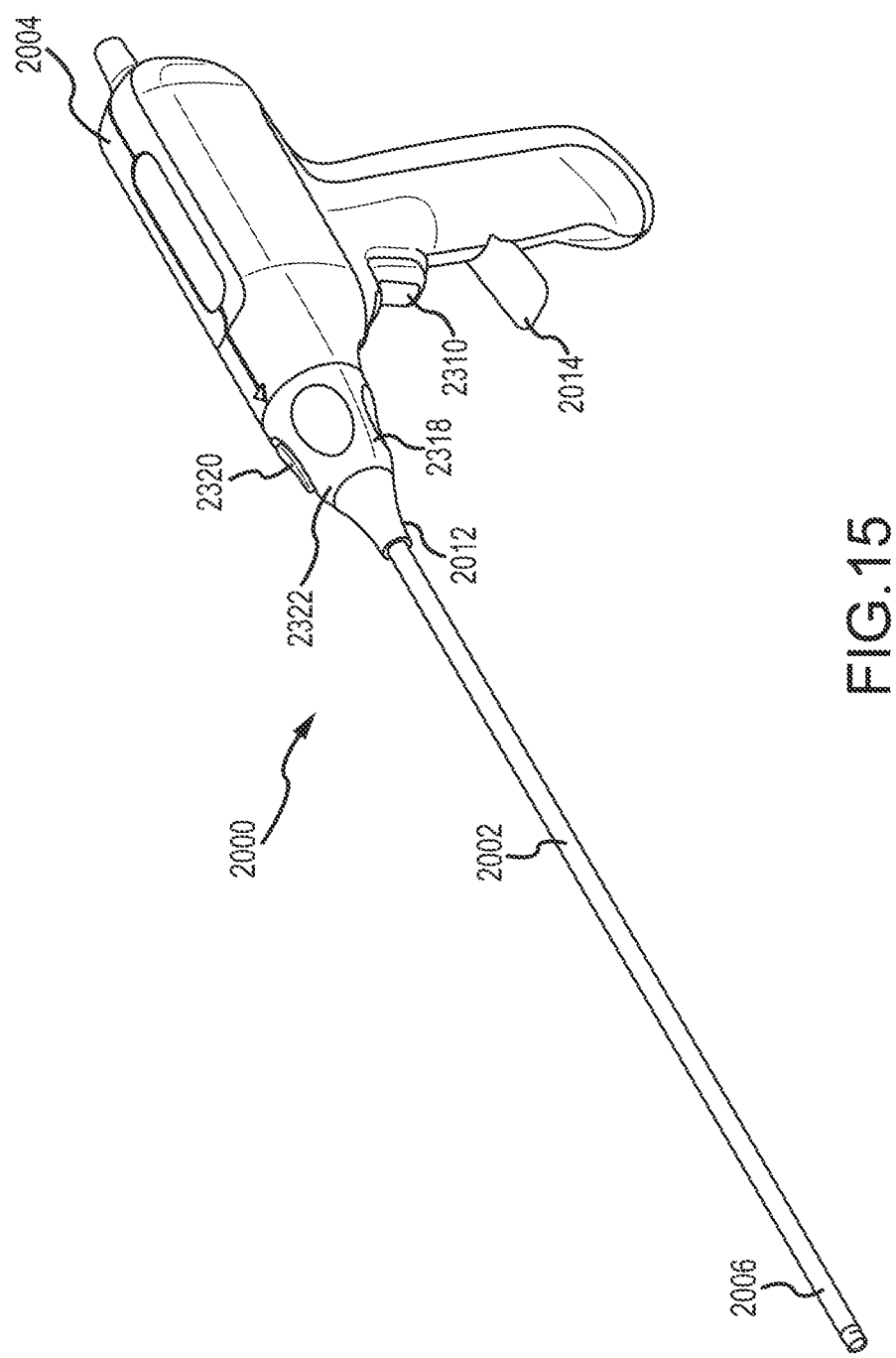
FIG. 15 is a perspective view of an alternative embodiment of a surgical device of the present disclosure.

Referring to FIG. 15, there is shown a perspective view of an alternative embodiment of a surgical device 2000 of the present disclosure. The surgical device 2000 is similar to the other surgical devices discussed hereinbefore, but surgical device 2000 is power driven by an electronic motor rather than utilizing manually actuation to rotate and translate the cutting tip, such as the manually actuated embodiment(s) shown in FIGS. 1-3. Therefore, for purposes of brevity, only the differences between the previously discussed surgical devices and surgical device 2000 will be described, and it shall be understood that surgical device 2000 may include the structures and components described earlier herein. For example, surgical device 2000 includes a sheath assembly 2002, which is similar to the sheath assembly 102 discussed herein before, particularly with respect to FIGS. 5A-5D. It shall be understood, that the sheath assembly 2002 of surgical device 2000 includes inner sheath assembly 542', intermediate sheath assembly 540' and outer sheath assembly 2006 similar to the sheath assembly 102 or assemblies of the other embodiment(s) of the surgical device(s) described earlier herein that inner sheath assembly 542, intermediate sheath assembly 540 and outer sheath assembly 106, respectively.

Figure 16:
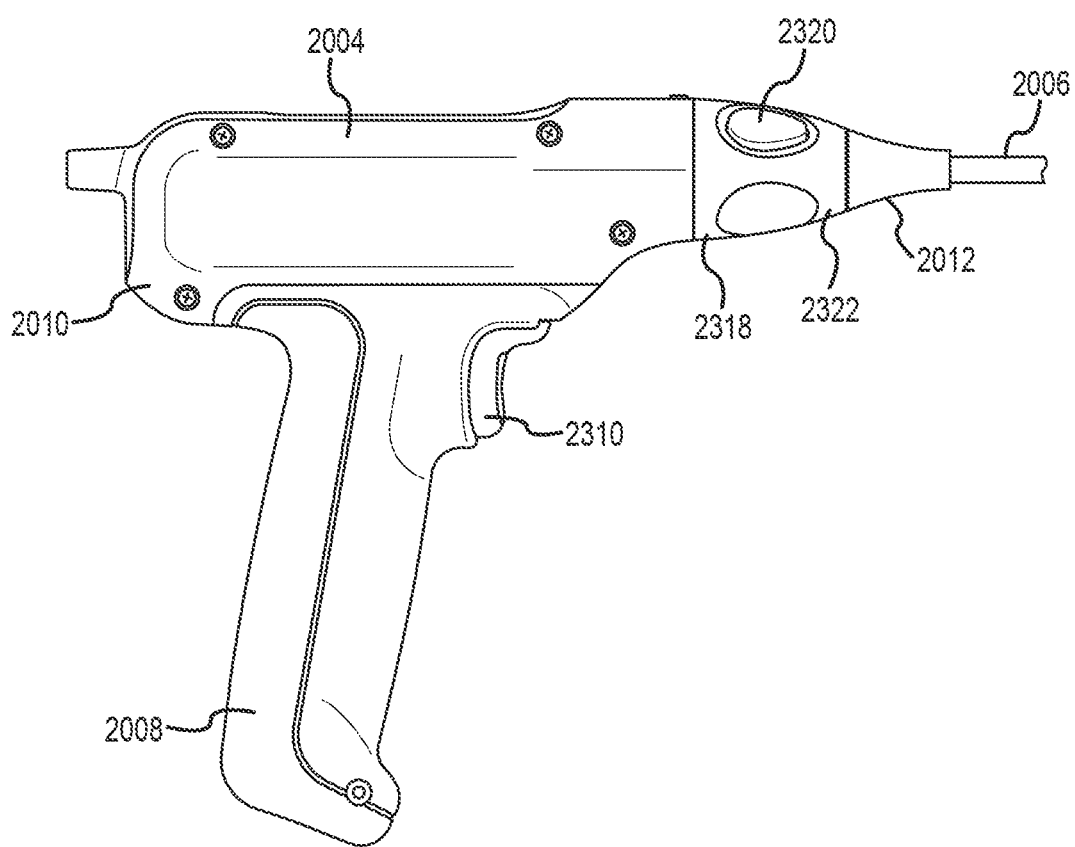
FIG. 16 is an elevation view of the surgical device illustrated in FIG. 15.

Referring to FIGS. 15 and 16, the surgical device 2000 may include a handle assembly 2004, a shield drive mechanism 2318 coupled to the handle assembly 2004, a strain relief 2012 extending from the shield drive mechanism 2318, and a sheath assembly 2002 coupled to and extending from the handle assembly 2004, the shield drive mechanism 2318 and the strain relief 2012. The handle assembly 2004 may include a top portion 2010, a bottom portion 2008, and a trigger (or trigger button) 2310 coupled to the bottom portion 2008. Although the trigger 2310 is illustrated as being coupled to the bottom portion 2008, it may be coupled to the top portion 2010 or another portion of the handle assembly 2004. The top portion 2010 and the bottom portion 2008 of the handle assembly 2004 may be integral or separate components. Additionally, the top portion 2010 and the bottom portion 2008 may overlap one another such that at least a portion of the bottom portion 2008 of the handle overlaps the top potion 2010, or vice versa.

Figure 17:
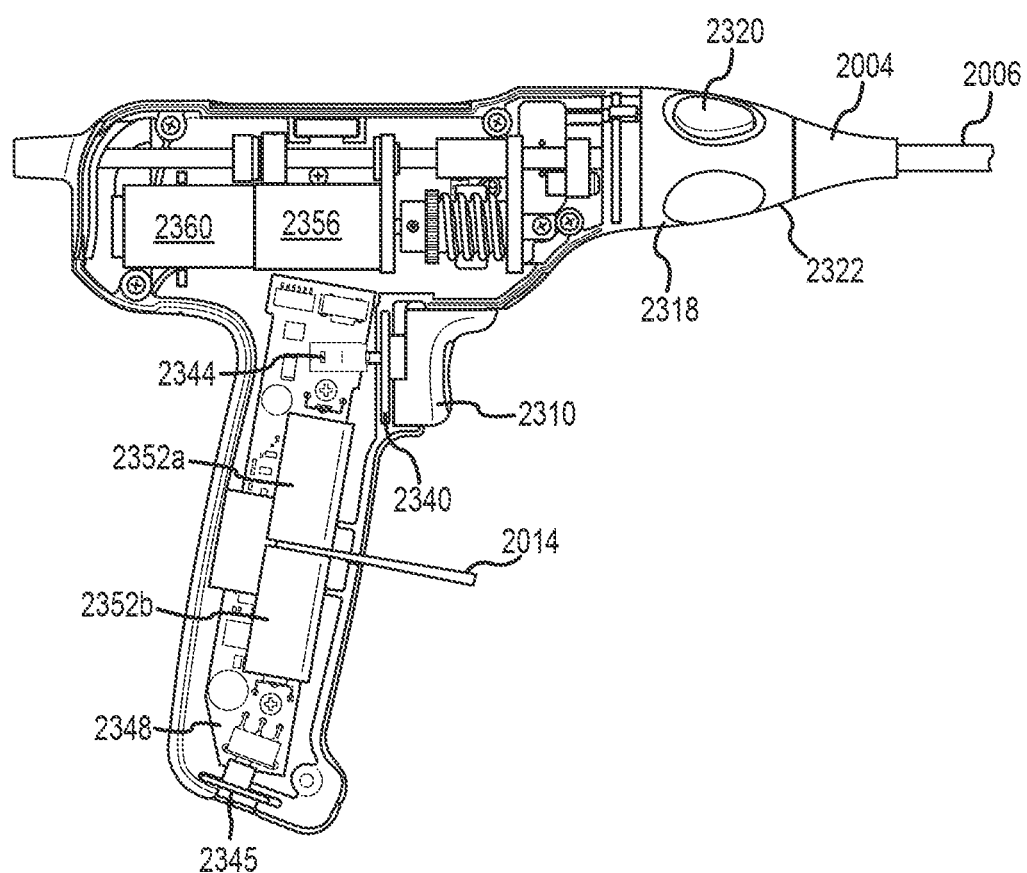
FIG. 17 is an internal view of a handle assembly of the surgical device illustrated in FIGS. 15 and 16.

Referring to FIG. 17, which is an internal view of the handle assembly 2004, there is shown a power switch 2345, a trigger switch 2344 coupled to the trigger 2310, a trigger seal 2340, one or more batteries 2352a, 2352b, a pull tab 2014 disposed between the batteries 2352a, 2352b, and a circuit board 2348 disposed within the bottom portion 2008 of the handle assembly 2004. Although these components are illustrated as being disposed within the bottom portion 2008, these components may be disposed within the top portion 2010 or another portion of the handle assembly 2004. Certain components of the cutting tip drive mechanism, which is disposed within the top portion 2010 of the handle assembly 2004 and includes motor 2360, is discussed in more detail below. Although the particular components of the cutting tip drive mechanism are illustrated as being disposed within the top portion 2010, these components may be disposed within the bottom portion 2008 or another portion of the handle assembly 2004.

The trigger switch 2344, the batteries 2352a, 2352b, the circuit board 2348 and the motor 2360 are electrically coupled to one another, thereby potentially forming a closed electrical circuit upon activation of the trigger switch 2344. The circuit board 2348 may include a controller 2404, which is discussed in more detail below with respect to FIG. 19. Generally, the controller 2404 may include one or more processors, memory and one more modules that contain logic or instructions stored in memory for controlling the operation of the surgical device 2000. For example, upon a clinician activating trigger 2310, the trigger switch 2344 is activated, thereby sending a signal to the controller 2404, which in turn allows the flow of current from the batteries 2352a, 2352b to the motor 2360 and activates the cutting tip drive mechanism. As illustrated in FIG. 17, there is a pull tab 2014 disposed between the batteries 2352a, 2352b, thereby opening the electrical circuit inhibiting the flow of current from the batteries 2352a, 2352b to the motor when the power switch 2345 is in the ON position. As such, a user of the surgical device 2000 must remove the pull tab 2014 prior to using the device 2000. Inclusion of the pull tab 2014 also may increase the battery life during shipment, storage and/or non-use of the surgical device 2000. Although the pull tab 2014 is disposed between the batteries 2352a, 2352b in this figure, the pull tab 2014 may be disposed in a different location to interrupt the electrical circuit formed between the trigger switch 2344, the batteries 2352a, 2352b, the circuit board 2348 and the motor 2360. Moreover, although the surgical device 2000 is illustrated and described as having batteries 2352a, 2352b as its power source or power supply, the surgical device 2000 may have an alternative power supply. For example, rather than having batteries 2352a, 2352b which produce direct current, the surgical device 2000 may be electrically coupled, via a coupler, to an auxiliary direct current or alternating current power supply.

Figure 17A:
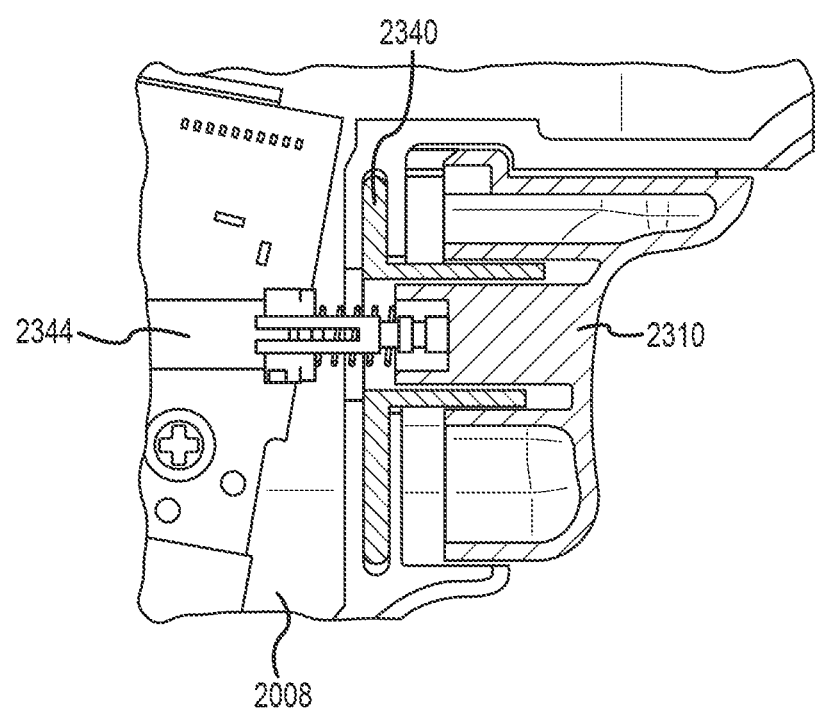
FIG. 17A is a longitudinal sectional view of the trigger illustrated in FIG. 17.

Referring to FIG. 17A, there is shown an enlarged cross-sectional view of the trigger 2310, trigger switch 2344 and a trigger seal 2340 disposed between the trigger 2310 and the housing for the bottom portion 2008 of the handle assembly 2004. During operation of the surgical device 2000, it desirable to limit and/or inhibit the entry and migration of body fluids, such as blood, from entering the handle assembly 2004 of the surgical device 2000 and contacting the electrical components, such as the trigger switch 2344, the batteries 2352a, 2352b, the circuit board 2348 and the motor 2360. The trigger seal 2340 may comprise or be constructed of various types of elastomeric materials (e.g., Pebax, Silicone, Nitrile, Polyurathanes, Flourocarbons and Perfluorinated elastomers) and foam. If the trigger seal 2340 comprises foam, it may be either an open-cell foam or a closed-cell foam.

Figure 17B:
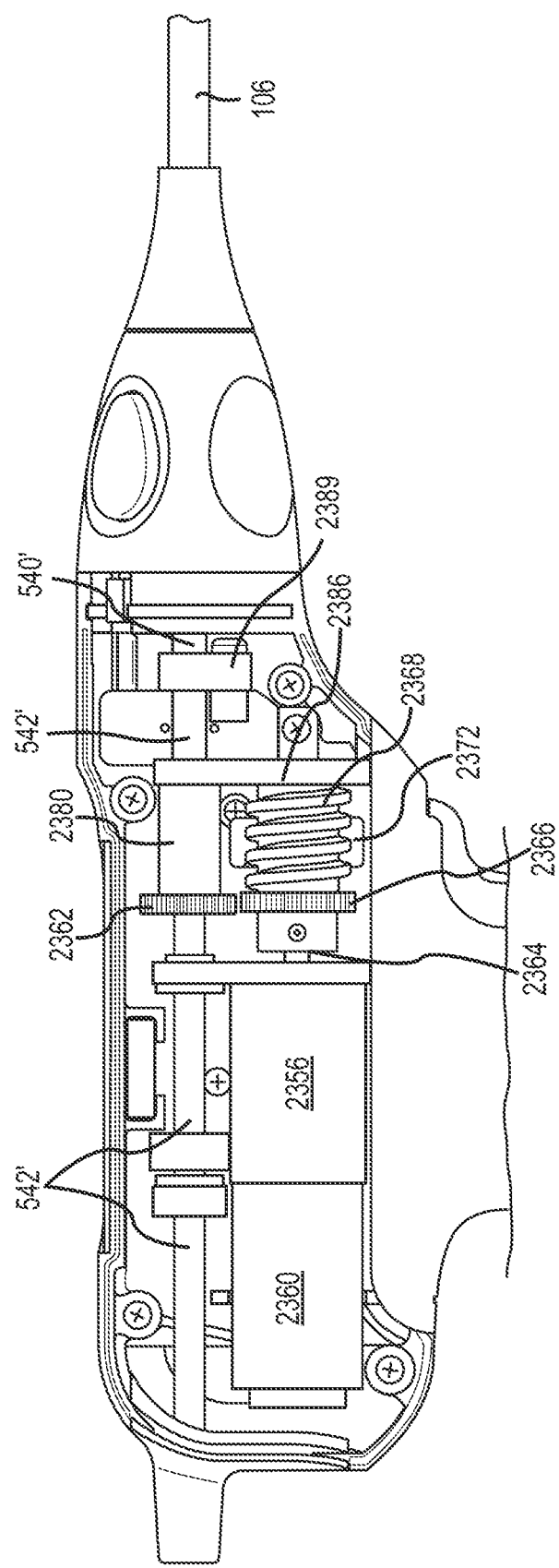
FIG. 17B is a longitudinal sectional view of the motor and gear assembly illustrated in FIG. 17.
Figure 17C:
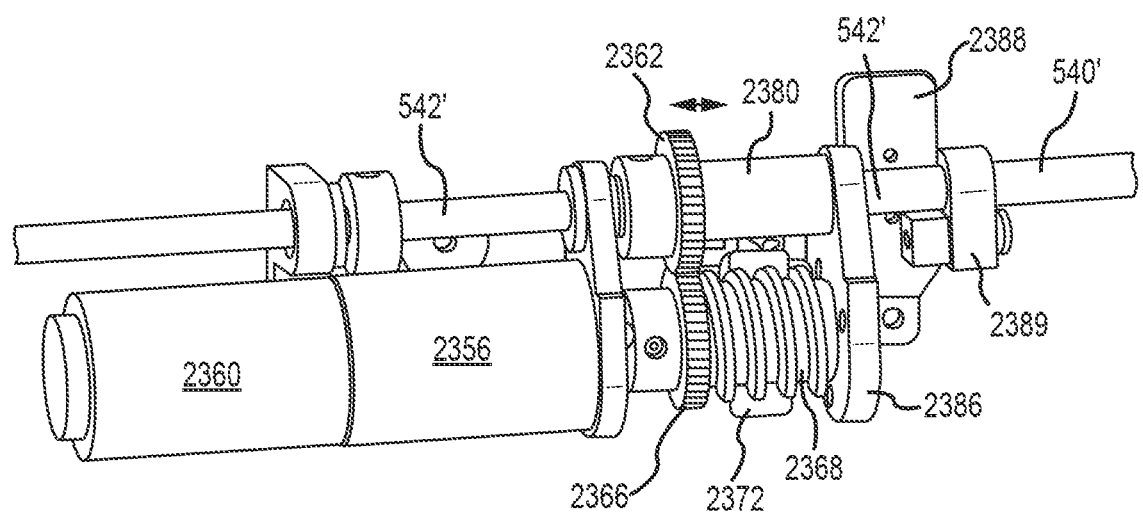
FIG. 17C is a perspective, assembled view of the motor and gear assembly illustrated in FIG. 17.
Figure 17D:
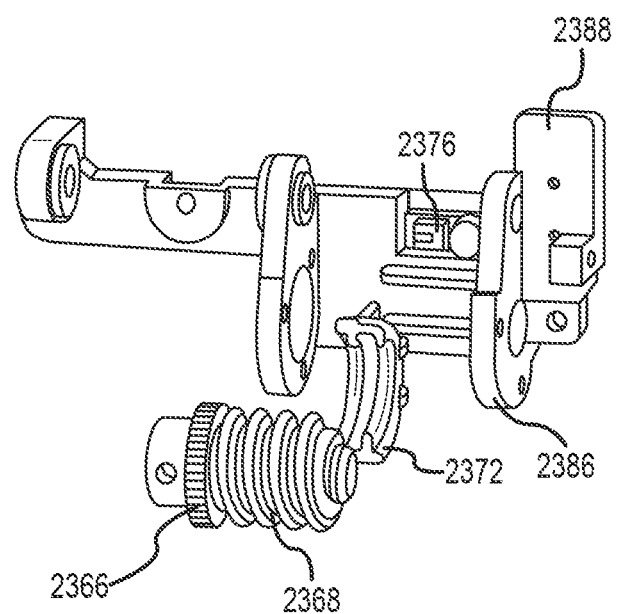
FIG. 17D is a perspective, disassembled view of the motor and gear assembly illustrated in FIG. 17.

Referring to FIGS. 17B, 17C, 17D, there is shown certain components of the cutting tip drive mechanism. For example, the cutting tip drive mechanism may include a motor 2360, a set of spur gears 2366, 2362, and inner sheath assembly 542' (or inner sheath). The motor 2360 may include encoder, a motor gearbox 2356, and a motor shaft 2364. The motor 2360 is coupled to spur gear 2366 via the motor gearbox 2356 and the motor shaft 2364. Spur gear 2366 is, in turn, coupled to spur gear 2362, which is coupled to the inner sheath assembly 542'. Upon rotation of the motor 2360 and motor shaft 2364, spur gear 2366 rotates and meshes with spur gear 2362. Because spur gear 2362 is coupled to the inner sheath assembly 542', which includes cutting tip 534', upon a clinician activating trigger 2310, the motor 2360, motor shaft 2364, spur gears 2366, 2362 rotate, thereby driving rotation of the inners sheath assembly 542' including the cutting tip drive mechanism. Although FIGS. 17B, 17C, 17D illustrate gears 2366, 2362 as spur gears, it shall be understood that other type of gear arrangements may be used, including but not limited to one or both gears being a helical gear, bevel gear, spiral gear, miter gear, worm gear, planetary gear, hypoid gear, rack and pinion, etc.

Referring to FIGS. 17B and 17C, spur gear 2366 is fixedly coupled to the motor shaft 2364. That is, spur gear 2366 is fixed to the motor shaft 2364 such that the spur gear 2366 and the motor shaft 2364 neither move axially nor rotate with respect to one another. Similarly, spur gear 2362 is fixedly coupled to the inner sheath of the inner sheath assembly 542' such that spur gear 2362 and the inner sheath 542' do not move either axially or rotationally with respect to one another. As discussed above, such as with respect to FIGS. 13 and 14, the inner sheath assembly is coupled to the intermediate sheath assembly by the cutting tip 1402 of the inner sheath assembly and the distal tip of the intermediate sheath assembly. For example, a pin is fixedly attached to the intermediate tip, and the pin sits within a cam slot of the inner sheath's cutting tip. As the inner sheath and cutting tip rotate, the cutting tip extends and retracts linearly with respect to the intermediate sheath and the outer sheath. Accordingly, the inner sheath inner sheath 542' rotates and axially translates with respect to the intermediate sheath 540'.

In order to accommodate for the axially translation of the inner sheath inner sheath 542' and the intermediate sheath 540', the spur gears 2366, 2362 are able to axially translate with respect to one another. For example, spur gear 2366 is axially fixed while rotating, and spur gear 2362 is able to translate axially while rotating. As long as the widths of the spur gears 2366, 2362 are wide enough, they will continue to mesh and engage one another during rotation, while compensating for the linear (longitudinal) translation of the inner sheath inner sheath 542' within the intermediate sheath 540' caused by the pin and cam slot interaction of the sheath assemblies.

An additional or alternative means of compensating for the linear translation of the inner sheath inner sheath 542' within the intermediate sheath 540' is similar to an inner key and outer key arrangement such as that disclosed and discussed in U.S. Provisional Application Ser. No. 61/947,377, filed Mar. 3, 2014, entitled MEDICAL DEVICE FOR REMOVING AN IMPLANTED OBJECT, which is hereby incorporated by reference. For example, FIG. 8 and FIG. 8C of that patent application illustrate an inner key of the inner sheath assembly located within an outer key of the outer sheath assembly, and the cross section of the exterior of proximal end of the inner key has a profile complimentary to the interior of the outer key. The inner key is able to rotate freely within the outer key due, at least in part, to the distal end of the exterior of the inner key having a circular cross section that mates with a circular cross section of the proximal end of a lumen within the outer key. Additionally, because the inner key and outer key are loosely coupled, the inner key and outer key are able to move longitudinally with respect to one another. For instance, supposing the outer key is fixed such that it neither rotates nor moves longitudinally, the inner key is able to both rotate and travel longitudinally within the outer key.

Referring to 17B and 17C of this disclosure, the surgical device 2000 may include a bracket or collet portion 2389 that serves as the outer key. The collet portion 2389 is fixedly attached to the proximal end of the intermediate sheath 540'. Accordingly, as the motor 2360 and motor shaft 2364 rotate, the spur gears 2366, 2362 mesh and rotate, thereby rotating the inner sheath 542' and the inner key within the intermediate sheath 540' and outer key 608. As mentioned above, in order to accommodate for the axially translation of the inner sheath inner sheath 542' and the intermediate sheath 540', the spur gears 2366, 2362 are able to axially (longitudinally) translate with respect to one another. And the cam slot profile in the cutting tip controls the longitudinal movement of the inner sheath assembly within the outer sheath assembly, including the longitudinal movement of the inner key relative to the outer key and the longitudinal movement of the cutting tip relative to the outer band.

Motor 2360, spur gears 2366, 2362, and inner sheath assembly 542' are supported by a bracket 2388 disposed within the top portion 2010 of the handle assembly 2004. And the cutting tip drive mechanism may also include a means for monitoring and/or determining the rotational and/or longitudinal position of the inner sheath assembly 542' and the cutting tip 534', particularly whether the inner sheath assembly 542' and the cutting tip 534' are in a home position (also referred to as non-extended position because the cutting tip 534' is in its most proximal axial position) and/or an extended position (because the cutting tip 534' is in a axial position distal of the home position). The means for monitoring and/or determining the rotational and/or longitudinal position of the inner sheath assembly 542' and the cutting tip 534' may include an acme screw or acme screw gear 2368 coupled to the motor 2360 via motor shaft 2364 and/or the spur gear 2366, a corresponding matingly-engaged acme nut 2372, and a position switch 2376 that is coupled to the bracket 2388. As the motor 2360, motor shaft 2364, spur gear 2366 rotate, the acme screw gear 2368 also rotates. As the acme screw gear 2368 rotates, it remains axially fixed along the longitudinal axis. Because the acme nut 2372 matingly engages the acme screw gear 2368, the acme nut 2372, which is not fixed, translates axially along the longitudinal axis as the acme screw gear 2368 rotates. The acme screw gear 2368 includes an engagement feature (not shown), which engages the position switch 2376 when the inner sheath assembly 542' and the cutting tip 534' are in their home position. The inner sheath assembly 542' and the cutting tip 534' are in their home position when they are axially in their most proximal position, such as the position in which the inner sheath assembly 542' and the cutting tip 534' are in prior to being rotated and longitudinally translated. That is, the inner sheath assembly 542' and the cutting tip 534' are in their home position when the acme nut 2372, inner sheath assembly 542' and the cutting tip 534' are in their most proximal position (non-extended position), such that the cutting tip 534' is in its most retracted position, regardless of whether the shield is in a shielded configuration or an extended configuration. Although FIG. 17D only illustrates one position switch (or sensor) 2376 indicative of the acme screw gear 2368, the inner sheath assembly 542' and the cutting tip 534' being in their home position, the surgical device 2000 may include additional position switches and/or position sensors indicative of the acme screw gear 2368, the inner sheath assembly 542' and the cutting tip 534' being in other positions, such one or more partially extended positions and/or extended positions.

When the inner sheath assembly 542' and the cutting tip 534' are in their home position and the engagement feature of the acme nut 2372 engages the position switch 2376, the switch 2376 produces a corresponding position signal and sends the position signal to the controller 2404. Although it is not shown, the surgical device 2000 may include additional position switches that monitor the longitudinal or axial position of the inner sheath assembly 542' and the cutting tip 534' upon the engagement feature engaging and triggering the additional position switches, which send corresponding position signals to the controller 2404. For example, the surgical device 2000 may include a position switch located at a position such that the engagement feature engages the position switch when the acme nut 2372, the inner sheath assembly 542' and the cutting tip 534' are in their most distal position (an extended position). Additional position switches may also be included to sense and monitor the position (of the acme nut 2372, the inner sheath assembly 542' and the cutting tip 534') between their most proximal and most distal positions. Alternatively, the one or more position switches may be replaced by one or more sensors that monitor(s) the longitudinal or axial position of the acme nut 2372, the inner sheath assembly 542' and the cutting tip 534', and the one or more sensors produce corresponding position signals to the controller 2404.

Referring to FIGS. 17B, 17C, 17D and 18, the acme nut 2372 (FIGS. 17B, 17C, and 17D) includes one or more protrusions 2390a, 2390b (FIG. 18) that engage with and slide within corresponding slots 2378a, 2378b, respectively. The slots 2378a, 2378b have proximal and distal ends. As such, the protrusions 2390a, 2390b and slots 2378a, 2378b serve as a means for limiting the axial or longitudinal movement of the acme nut 2372, the inner sheath assembly 542' and the cutting tip 534'. That is, upon the protrusion 2390a abutting and contacting the distal end of slot 2378a, the acme nut 2372, the inner sheath assembly 542' and the cutting tip 534' are inhibited from moving further distally. Similarly, upon the protrusion 2390b abutting and contacting the proximal end of slot 2378b, the acme nut 2372, the inner sheath assembly 542' and the cutting tip 534' are inhibited from moving further proximally. As such, the axial or longitudinal movement of the acme nut 2372, the inner sheath assembly 542' and the cutting tip 534' are limited by the length of the slots 2378a, 2378b. Other or alternative means for limiting the axial or longitudinal movement of the acme nut 2372, the inner sheath assembly 542' and the cutting tip 534' may be included in the surgical device 2000. For example, bracket portion 2386 may serve as an abutment, which the acme nut 2372 abuts and contacts when the acme nut 2372, the inner sheath assembly 542' and the cutting tip 534' are in their most distal positions. Although not shown, the bracket 2388 may include another abutment that the acme nut 2372 abuts and contacts when the acme nut 2372, the inner sheath assembly 542' and the cutting tip 534' are in their most proximal positions.

When the acme nut 2372 contacts the means for limiting the axial or longitudinal movement of the acme nut 2372, current supplied to the motor may increase. The controller 2404 monitors such current, and upon the current exceeding a predetermined threshold, the supply of power to the motor is discontinued, thereby stopping and inhibiting further rotation and translation of the cutting tip drive mechanism and the inner sheath assembly 542' and the cutting tip 534'. The acme screw gear 2368 and the acme nut 2372 can also be configured to increase or decrease the amount of current used to rotate the screw gear 2368. For example, the size and pitch of the threads of the acme screw gear 2368 and the acme nut 2372 may be fixed or variable such that the current increases or decreases with rotation of the screw gear 2368.

Figure 18:
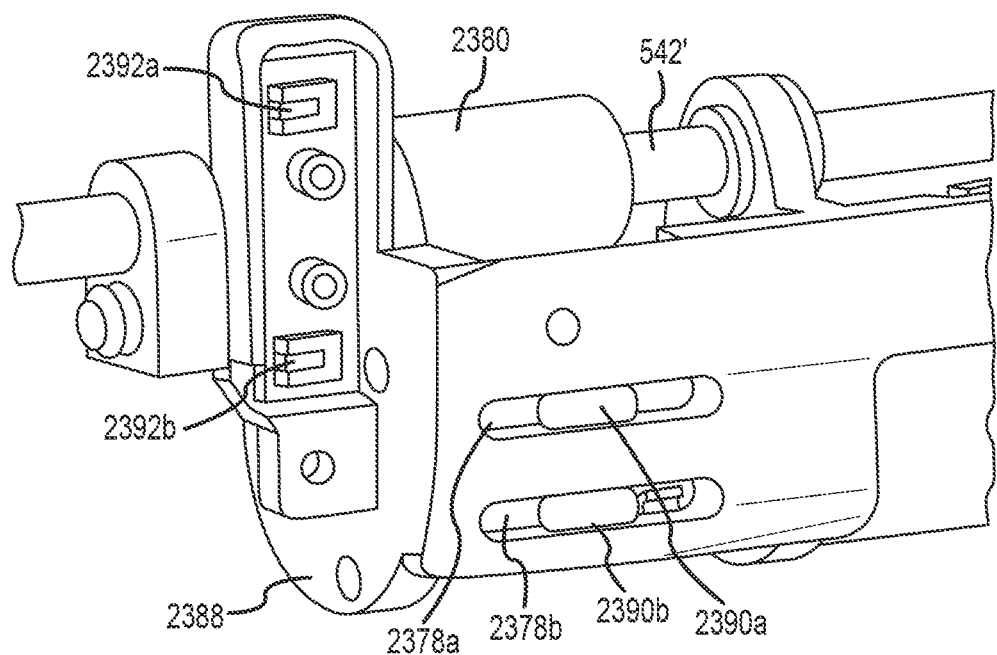
FIG. 18 is an enlarged, perspective view of a switch assembly.

Referring to FIGS. 17C and 18, there is shown a seal member 2380 that is disposed adjacent and proximally of the bracket portion 2386 and adjacent and proximally of spur gear 2362. That is, seal member 2380 is disposed between spur gear 2362 and bracket portion 2386. As mentioned above, during operation of the surgical device 2000, it desirable to limit and/or inhibit the entry and migration of body fluids, such as blood, from entering the handle assembly 2004, and seal member 2380 aids in such limitation and/or inhibition. Seal member 2380 may comprise or be constructed of the same or similar materials that trigger seal 2340 comprises. The seal member 2380 is configured to surround the sheath assembly 2002, particularly the inner sheath assembly 542' and/or the intermediate sheath assembly 540'.

Figure 20A:
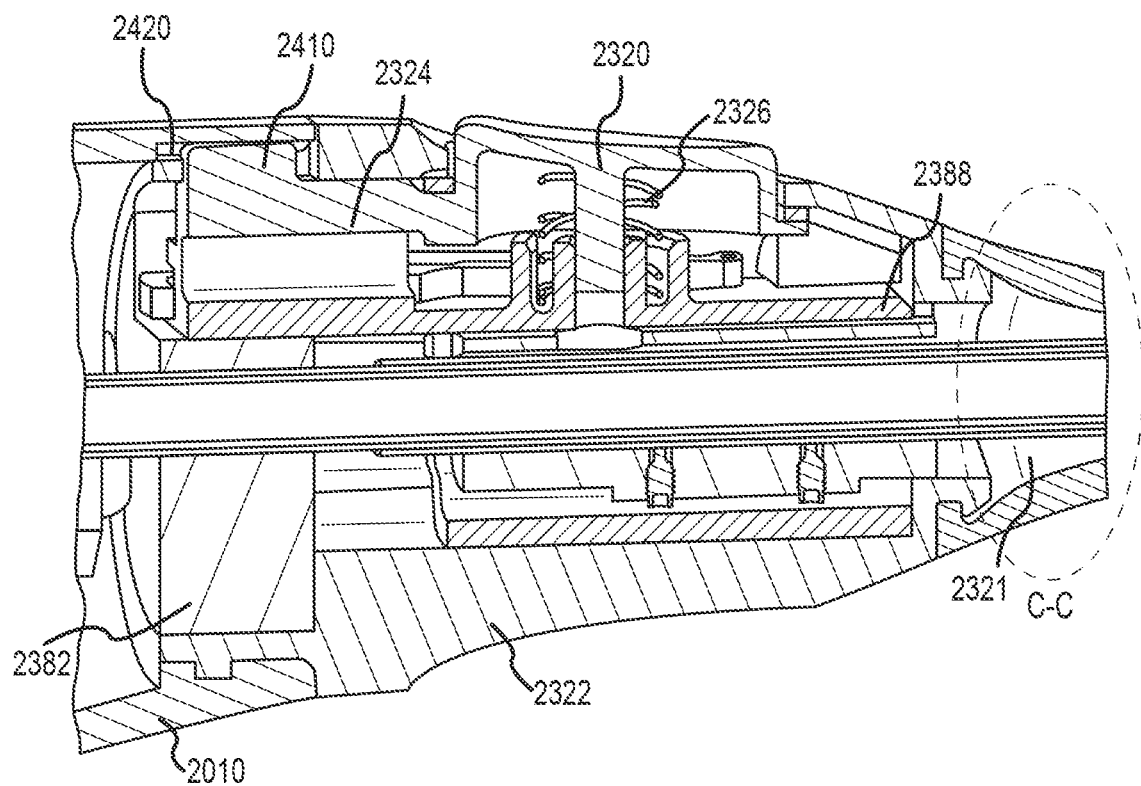
FIG. 20A is a longitudinal sectional view of an alternative embodiment of a shield drive mechanism for the surgical device illustrated in FIG. 15.
Figure 20B:
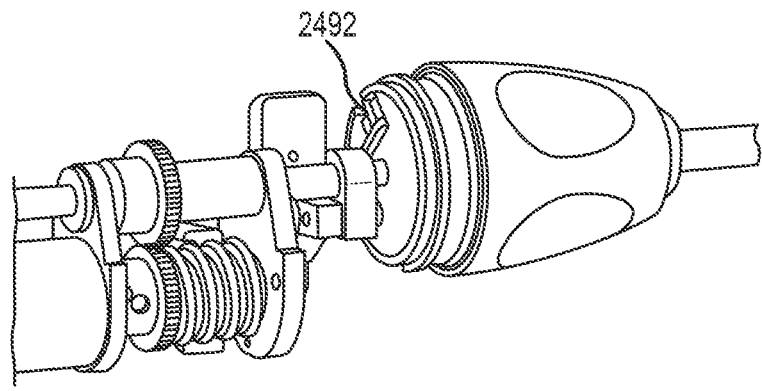
FIG. 20B is a perspective, disassembled view of the shield drive mechanism for the surgical device illustrated in FIG. 15.
Figure 20C:
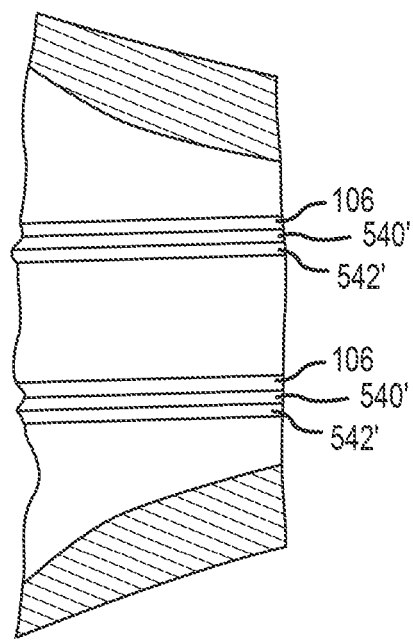
FIG. 20C is an enlarged view of the distal portion of the knob illustrated in FIG. 20A.

Referring to FIG. 20A and FIG. 20C, there is shown a cross-sectional view of the shield drive mechanism 2318. Shield drive mechanism 2318 may include a knob 2322 (or chuck), a button 2320, a support member 2328 and a spring 2326 disposed between the knob 2322 and the support member 2388. The support member 2388 is disposed radially and internally of the knob 2322, and the support member 2388 includes a lumen there through for passage of the inner sheath assembly 542' and/or the intermediate sheath assembly 540'. The button 2320 includes an arm 2324 that has a detent, such that in its released state, the spring 2326 forces the button 2320 and the arm 2324 radially outward, and the detent 2410 engages a recess 2420 in the housing for the top portion 2010 of the handle assembly 2004. When the detent 2410 engages the recess 2420, the knob 2322 is maintained in a non-rotational orientation relative to the handle assembly 2004. That is, when the detent 2410 engages the recess 2420, the knob 2322 is unable to rotate. Upon depression of the button 2320, the detent 2410 disengages the recess 2420, thereby allowing rotation of the knob 2322. The knob 2322 (or chuck), the button 2320, the support member 2328, the spring 2326 or any combination thereof cooperate to provide a means for preventing or minimizing the likelihood of inadvertent movement of the position of the shield drive mechanism 2318, particularly during use of the surgical device 2000. Although the present disclosure only discloses this means for preventing or minimizing the likelihood of inadvertent movement of the position of the shield drive mechanism, other means are contemplated, such as a switch or other lock mechanism that would have to be engaged or disengaged to allow rotation and translation of outer sheath assembly and/or the shield drive mechanism. Furthermore, the shield drive mechanism may be moveable from one position to another position upon linear translation only.

Although they are not shown in FIG. 20A, the top portion 2010 of the handle assembly 2004 may include a plurality of recesses that correspond to a shielded configuration, an extended configuration and/or plurality of shielded configurations and extended configurations for the surgical device 2000. That is, upon depression of the button 2320, the knob 2322 may be rotated until the knob 2322 reaches a rotational position that will allow the detent 2410 engage a recess 2420 indicative of another configuration for the shield and/or shield drive mechanism, similar to the configurations discussed with respect to FIGS. 4A, and 4B herein before, such as a "shielded rotational orientation", "partially extended rotational orientation", "fully extended configuration" or some other shielded or extended configuration.

Continuing to refer to FIG. 20A, there is shown the inner sheath assembly 542', the intermediate sheath assembly 540', and the outer sheath assembly 106. The outer sheath assembly 106 is fixedly attached to the knob 2322 via a slidable outer sheath collet 2388, which is slidable relative to the knob 2322. The intermediate sheath assembly 540' is fixed, as discussed hereinbefore, but both the outer sheath assembly 106 and inner sheath assembly 542' rotate and translate longitudinally relative to the intermediate sheath assembly 540'.

A seal member 2382 may also be disposed adjacent and distally of the bracket portion 2386 and adjacent and proximal the proximal end of the knob 2322. That is, seal member 2382 is disposed between the proximal end of the knob 2322 and bracket portion 2386. As mentioned above, during operation of the surgical device 2000, it desirable to limit and/or inhibit the entry and migration of body fluids, such as blood, from entering the handle assembly 2004, and seal member 2382 aids in such limitation and/or inhibition. Seal member 2382 may comprise or be constructed of the same or similar materials that trigger seal 2340 and/or seal member 2380 comprise. The seal member 2382 is configured to surround the sheath assembly 2002, particularly the outer sheath assembly 106 and/or the intermediate sheath assembly 540'.

Referring to FIG. 18, there is depicted is an enlarged, perspective view of a switch assembly and/or a sensor assembly that includes one or more switches 2392a, 2392b or sensors that determine whether the shield mechanism is in a "shielded rotational orientation" or an "extended rotational orientation." The knob 2322 includes an engagement feature 2492 (FIG. 20B) that interacts with the one or more switches 2392a, 2392b when the knob 2322 and shield drive mechanism are in a "shielded rotational orientation" or an "extended rotational orientation." Upon the switches 2392a, 2392b or sensors determining and/or sensing that the shield mechanism is in a "shielded rotational orientation" or an "extended rotational orientation," the switches 2392a, 2392b or sensors will send corresponding shield position signals to the controller 2404. Although FIG. 18 only illustrates two switches 2392a, 2392b, it shall be understood the surgical device may have additional switches or sensors indicative of and corresponding to additional shielded positions and/or extended positions. Similar to the chuck 322 in FIGS. 4A and 4B, the shield drive mechanism, particularly the knob 2322, may include one or more indicators that align with an indicator on the top portion 2010 of the handle assembly 2004, thereby indicating that the shield drive mechanism and the shield are in one of the shielded configuration(s) or one of the extended configuration(s).

Figure 21:
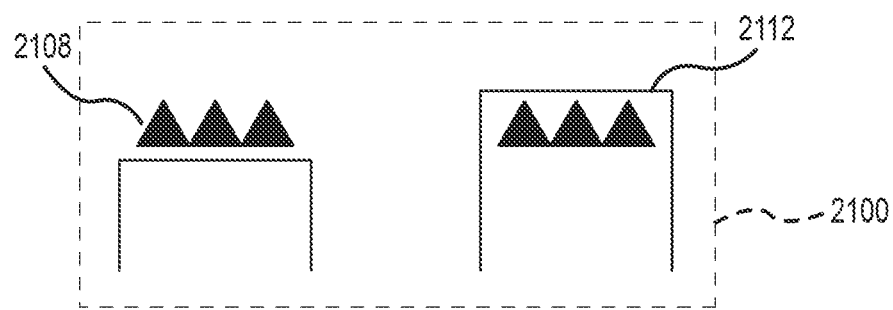
FIG. 21 is an illustration of two icons that can be displayed on a graphical user interface.

Additionally, although it is not shown in the figures, the indicators may alternatively include electronic visual indicators that are incorporated on the handle assembly 2104. For example, the surgical device 2000 may include multiple light emitting diodes 2416, which are illuminated when the shield drive mechanism and/or the shield are in one of the shielded configuration(s) or one of the extended configuration(s). Also, referring to FIG. 21, the surgical device 2000 may also include a graphical user interface 2100 that is coupled to or disposed on the handle assembly 2104. The graphical user interface 2100 may display an indicator and/or an icon 2108, 2112 that is illustrative of whether that the shield drive mechanism and the shield are in one of the shielded configuration(s) or one of the extended configuration(s). Although it is not shown, another type of indicator indicative of the position of the shield—either retracted or extended—includes audible signals. That is, there can be different audible signals indicative of whether the shield drive mechanism and the shield are in one of the shielded configuration(s) or one of the extended configuration(s).

Figure 19A:
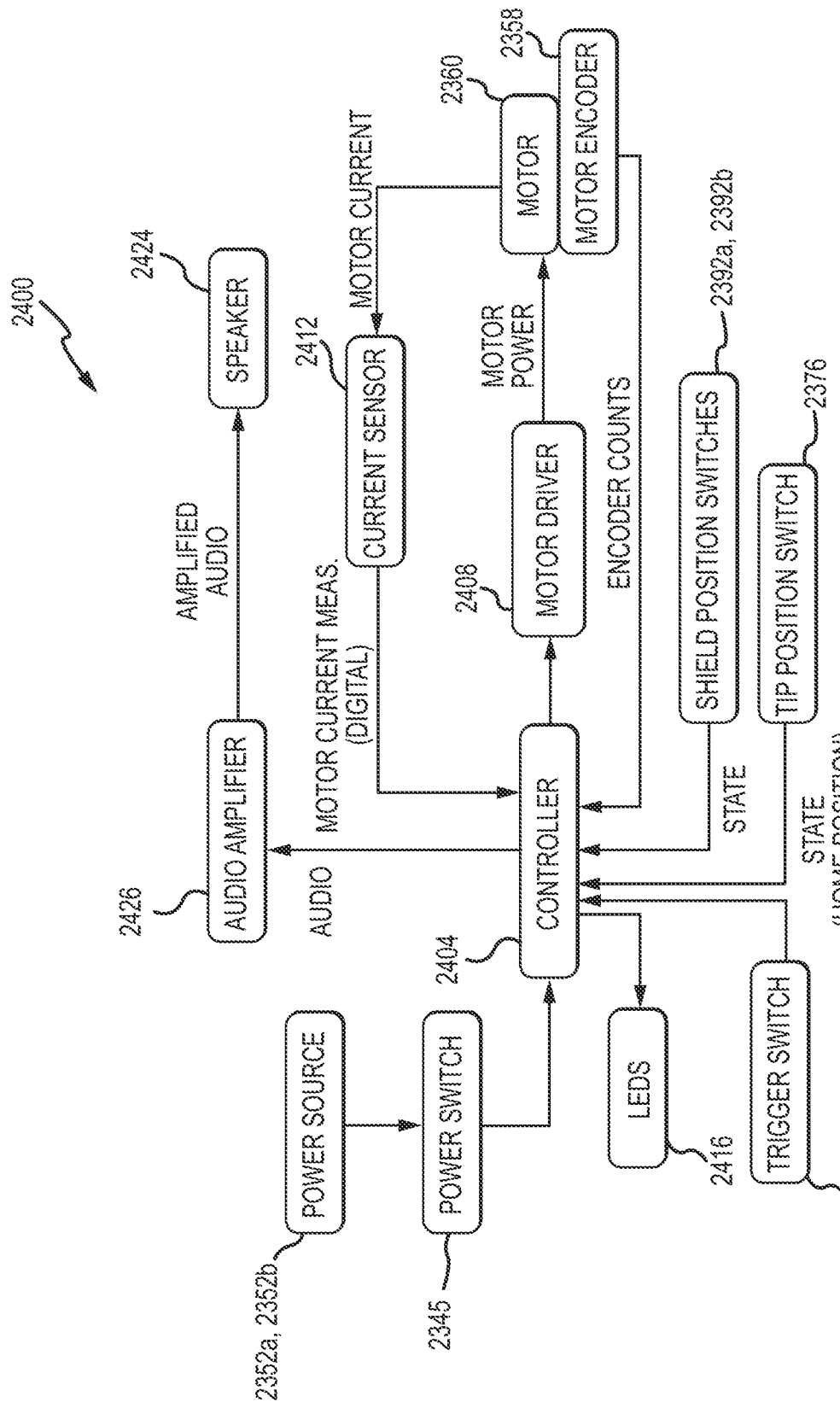
FIG. 19A is a depiction of a block diagram of a control system for the surgical device illustrated in FIG. 15.

Referring to FIG. 19A, there is depicted a block diagram of a control system 2400 for the surgical device 2000. The control system 2400 may comprise a controller 2404 that includes one or more processors, memory and one more modules that contain logic or instructions stored in memory for controlling the operation of the surgical device 2000. For example, the instructions may be stored in memory, such as non-transitory computer-readable medium, and the processor executes the instructions.

Figure 19B:
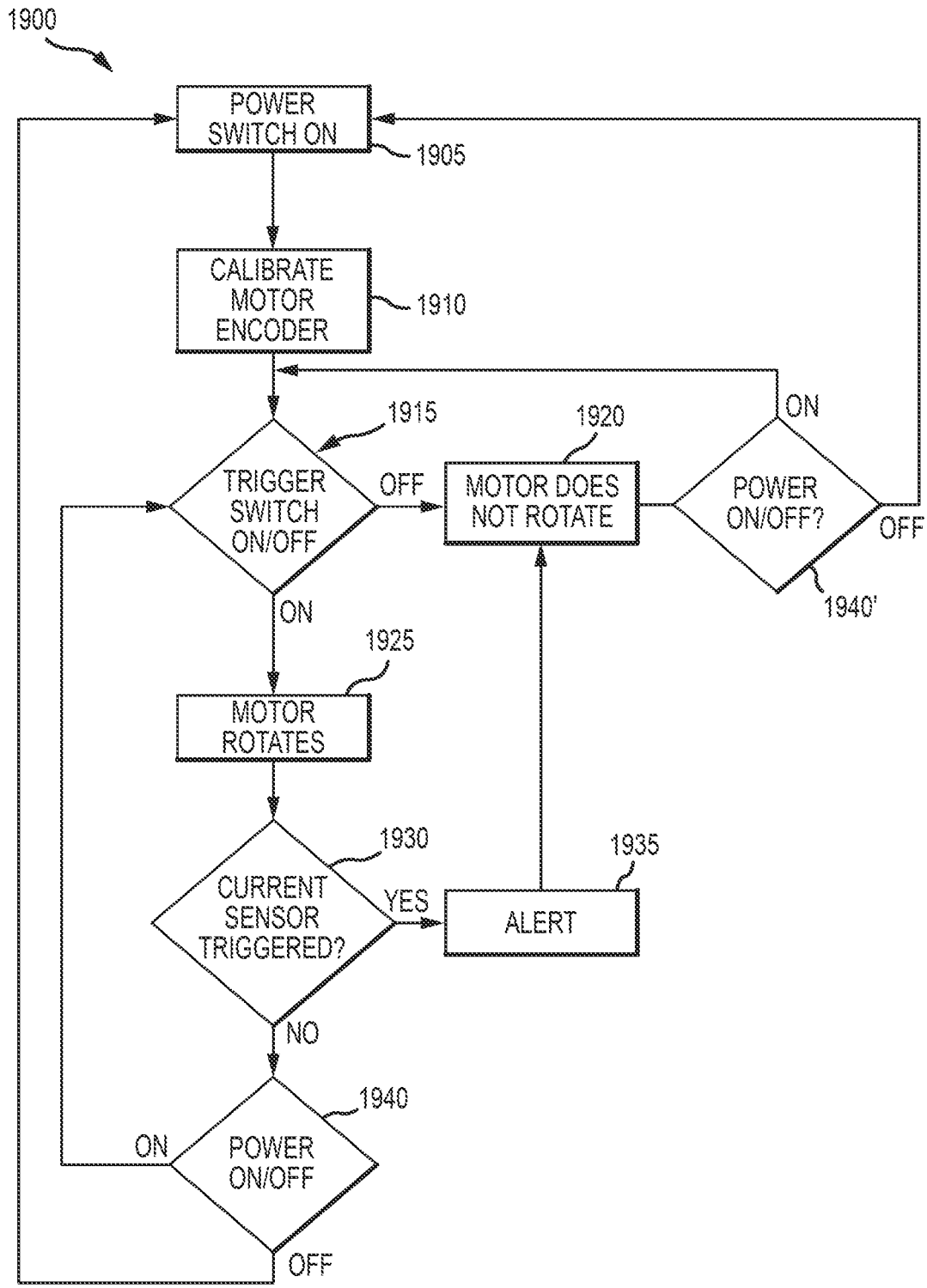
FIG. 19B is a flow chart that depicts a portion of the logic that is used in conjunction with the control system depicted in FIG. 19A.

Upon the user of the surgical device 2000 removing the pull tab 2014 from the surgical device 2000 and actuating the power switch 2345 to be in the ON position, power is able to flow from the power source, such as one or more disposed between the batteries 2352a, 2352b, to the controller 2345. Referring to FIG. 19B, there is shown a flow chart that depicts a portion of the logic 1900 that is used in conjunction with the control system 2400 to operate the surgical device 2000, including rotation of the inner sheath assembly 542' and the cutting tip. For example, the operational control logic 1900 may include receiving a signal that the power switch 2345 is in the ON position 1905. The operational control logic 1900 may also determine whether the power switch 2345 is in the ON position 1905 for the first time after the power switch 2345 being in the OFF position. If the power switch 2345 is in the ON position 1905 after being in the OFF position, then the operational control logic 1900 may automatically initiate a motor encoder calibration routine 1910, which is discussed in more detail below in conjunction with FIG. 19C.

After calibrating the motor encoder by using the motor encoder calibration routine 1910, the operational control logic 1900 will determine whether the trigger switch 2310 is in the ON position or the OFF position 1915. If the trigger switch 2310 is in the OFF position, then the motor 2360 does not rotate 1920. If, however, the trigger switch 2310 is in the ON position, then the motor 2360 rotates 1925, as long as the trigger switch 2310 continues to remain in such position and the current sensor 2412 does not produce and send a signal to the controller 2404 indicative of the motor current exceeding a predetermined threshold 1930. Assuming the current sensor 2412 does not produce and send a signal to the controller 2404 indicative of the motor current exceeding a predetermined threshold 1930, the motor 2360 may continuously rotate in one direction (i.e., clockwise) or in another direction (i.e., counter-clockwise) while the trigger switch 2310 is in the ON position, thereby rotating and/or translating the inner sheath and cutting tip. Alternatively or additionally, the operational control logic 1900 may include instructions to alternate the direction of the rotation of the motor (and rotation and/or translation of the inner sheath and cutting tip) from one direction to another direction after rotating a predetermined number of rotations in a particular direction. For example, upon actuating the trigger switch 2310 to the ON position, the motor 2360 (and the inner sheath and the cutting tip) may initially rotate in one direction (i.e., clockwise) for a predetermined number of revolutions (e.g., 1, 2, 3, 4, 5, 6, 7, 8, 9, 10, etc.), and subsequently stop and rotate or in the reverse direction (i.e., counter-clockwise) for a predetermined number of revolutions (e.g., 1, 2, 3, 4, 5, 6, 7, 8, 9, 10, etc.). The predetermined number of revolutions with which the motor 2360 (and the inner sheath and the cutting tip) initially rotates in one direction may be less than, the same or more than the motor 2360 rotates in the opposite direction.

If the current sensor 2412 produces a signal indicative of the motor current exceeding a predetermined threshold, then the controller 2404 produces an alert 1935 and the supply of power to the motor 2360 is discontinued, thereby discontinuing motor rotation 1920. If the current sensor 2412 does not produces a signal indicative of the motor current exceeding a predetermined threshold or the current sensor 2412 produces a signal indicative of the motor current being less than a predetermined threshold, then the controller 2404 allows the motor to rotate until the trigger switch 2310 is actuated from the ON position to the OFF position 1940, at which time motor movement stops. In order for the motor to begin rotating again, the operator need only actuate the trigger switch 2310 again, while the power switch 2345 remains in the ON position. If the power switch 2345 is switched from the ON position to the ON position 1905, then the power switch 2345 must be actuated to the ON position 1905, and upon such actuation, the motor encoder calibration routine 1910 is re-run.

The description included above refers to using a current sensor 2412 that produces a signal indicative of the motor current exceeding a predetermined threshold. It shall be understood that the current sensor 2412 may be replaced with one or more limit switches. Moreover, there may be alternative means of producing a signal indicative of the motor current exceeding a predetermined threshold.

Figure 19C:
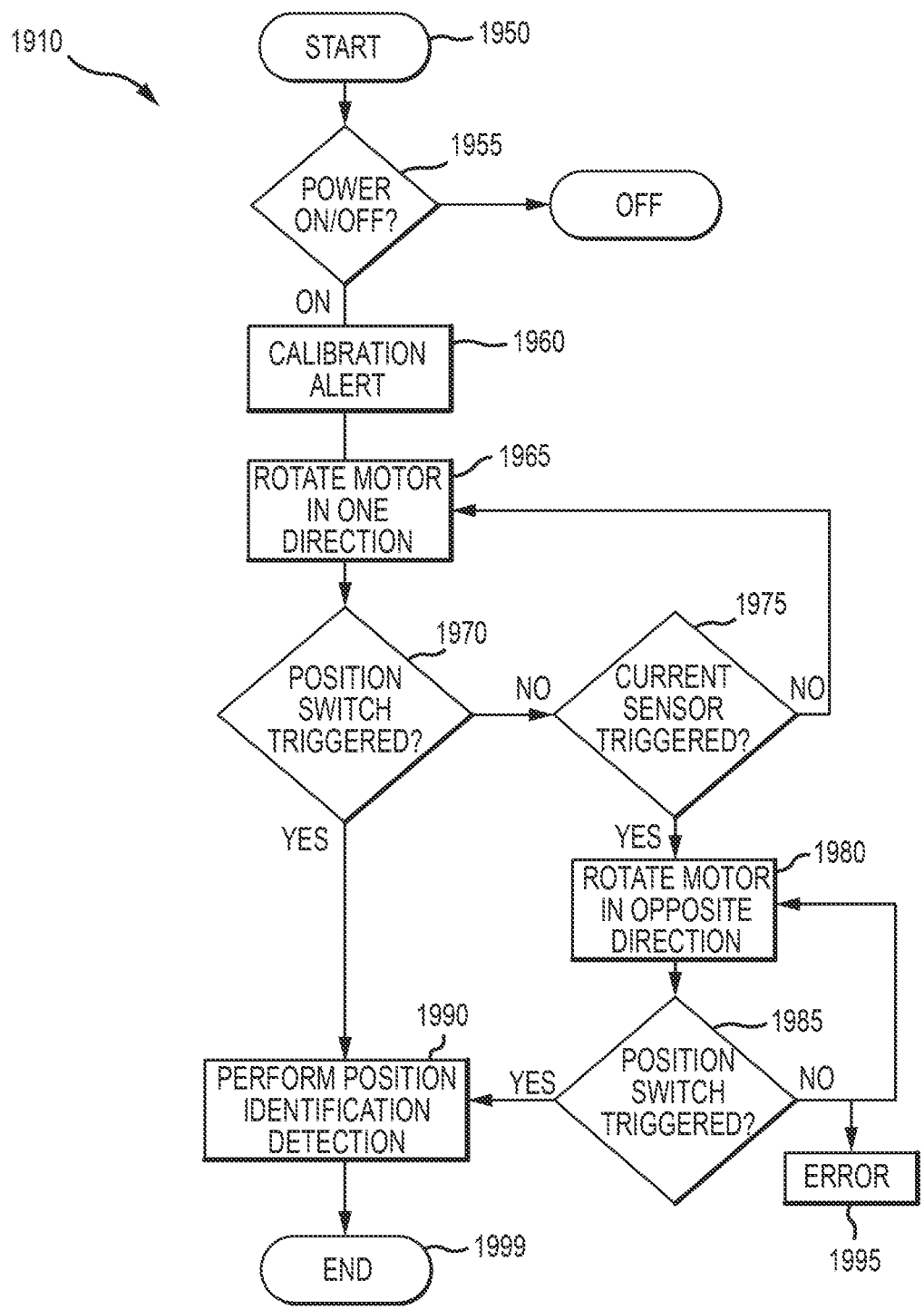
FIG. 19C is a flow chart that depicts the logic associated with calibrating the motor encoder step in the control system depicted in FIG. 19B.

Referring to FIG. 19C, there is shown a flow chart depicting an example of a motor encoder calibration routine 1910. The routine 1910 starts 1950 by determining whether the power switch 2345 is in the ON position and/or the power source 2352a, 2352b is providing power to the motor 2368 and/or the controller 2404, as shown in decision block 1955. If the power switch 2345 is in the ON position and/or the power source 2352a, 2352b is providing power to the motor 2368 and/or the controller 2404, then the controller 2404 produces an alert 1960 indicating to the user of the device 2000 that the device is performing a calibration step. The logic is designed and configured such that during the calibration routine 1910, a user cannot actuate the trigger switch 2310 or activate the motor 2368 via the trigger switch 2310. Alternatively, rather than initiating the calibration routine 1910 upon powering the motor 2368 and/or the controller 2404, the calibration routine 1910 may be initiated after powering the motor 2368 and/or the controller 2404 and upon the user of the device engaging the trigger 2310 or some other engagement feature.

The calibration routine 1910 includes a step 1965 of rotating the motor 2368 in an initial direction—either a clockwise or counter-clockwise direction—as shown in block 2365. While motor 2368 is rotating, the calibration routine 1910 and controller 2404 determine whether the position switch(es) 2376 or sensor(s) have been triggered, as shown in decision block 1970. As long as the current sensor 2412 is not triggered 1975, the motor continues to rotate in the initial direction until the position switch is triggered. When the position switch(es) 2376 or sensor(s) are triggered, such triggering is indicative of the motor 2368 and motor shaft 2364 and inner sheath assembly and cutting tip being in their home position(s). And upon identifying the home position, the motor encoder is calibrated or re-calibrated such that the home position corresponds to a zero position for the motor encoder.

The calibration routine 1910 may also include the optional step of performing an additional position identification detection routine 1990 to confirm the zero calibration position of the motor encoder. Such additional position identification detection routine 1990 may include rotating the motor 2368 and motor shaft 2364 in either or both a clockwise and counter-clockwise direction a certain number of predetermined rotations, and then rotating the motor 2368 and motor shaft 2364 in an opposite direction the same number of predetermined rotations to confirm that upon completion of such opposite rotations, the position switch(es) 2376 or sensor(s) are again triggered, thereby indicating that the motor 2368 and motor shaft 2364 have returned to their home position(s). At this point, the calibration routine 1910 is complete, and the motor encoder, motor shaft, position switch(es) are calibrated, such that the user of the surgical device 2000 can activate the triggers switch 2344 and actuate rotation of the cutting tip via the remainder of the logic 1900 in FIG. 19B.

Referring again to FIG. 19C, if the calibration routine 1910 and controller 2404 determine that the position switch(es) 2376 or sensor(s) are not triggered upon rotating the motor 2368 in an initial direction, as shown in decision block 1970, and the current sensor 2412 is triggered, then the motor 2368 is stopped, and the controller 2404 rotates the motor in the opposite direction, as shown in decision block 1975 and block 1980. As long as the current sensor 2412 is not triggered 1975, the motor continues to rotate in the opposite direction until the position switch 2376 is triggered, as shown in block 1985. When the position switch 2376 or sensor is triggered, such triggering is indicative of the motor 2368 and motor shaft 2364 and inner sheath assembly and cutting tip being in their home position(s). And upon identifying the home position, the motor encoder is calibrated or re-calibrated such that the home position corresponds to a zero position for the motor encoder.

The description included above discusses using the calibration routine 1910 upon powering of the device. The calibration routine 1910 may also or alternatively be initiated and/or used after the controller logic receives an error signal. Additionally, the calibration routine 1910 may be used to confirm or re-confirm the position of the motor, the inner sheath and/or the cutting tip, such as determining whether the motor, the inner sheath and/or the cutting tip are in a particular longitudinal and/or rotational position. For example, it may be desirable during use of the device for the user to re-calibrate the device at certain times during use in order to ensure the clinician knows the location of the cutter, and whether the motor, the inner sheath and/or the cutting tip are in a particular position, such as a home position (e.g., fully retracted) or another position (e.g., partially retracted, partially extended or fully extended).

Referring again to FIG. 19C, an alternative calibration routine may include a routine similar to that shown in this figure but with the step of the "current sensor triggered" 1975 being omitted. For example, the calibration routine may include a step 1965 of rotating the motor 2368 in an initial direction—either a clockwise or counter-clockwise direction—as shown in block 2365. While motor 2368 is rotating, the calibration routine 1910 and controller 2404 determine whether the position switch(es) 2376 or sensor(s) have been triggered, as shown in decision block 1970. Upon the position switch(es) 2376 or sensor(s) are triggered, such triggering is indicative of the motor 2368 and motor shaft 2364 and inner sheath assembly and cutting tip being in their home position(s). The controller then 2404 rotates the motor in the opposite direction to determine when the position switch is triggered in the opposite, as shown in blocks 1980 and 1985. Blocks 1980 and 1985 would be located after block 1965 and prior to block 1990.

Referring again to FIG. 19A, as discussed above, the surgical device 2000 includes a shield drive mechanism that may be actuated by the user of the surgical device 2000 to reconfigure the device from a shielded configuration (that is, a configuration in which the cutting tip is disposed within the outer sheath assembly) to an extended configuration (that is, a configuration in which the cutting tip at least partially protrudes from the outer sheath assembly) and vice versa. The surgical device, may also include a switch assembly and/or a sensor assembly that includes one or more switches 2392a, 2392b or sensors that sense and determine the whether the shield mechanism is in a "shielded rotational orientation" or an "extended rotational orientation" and the switches 2392a, 2392b or sensors produce and send corresponding shield position signals to the controller 2404.

Upon the controller 2404 receiving the shield position signals, the controller may send an alert signal indicative of the shield and/or shield drive mechanism being in one of a shielded configuration or an extended configuration, thereby informing the user of the device that upon actuation of the trigger, the cutting tip will either remain or at least partially protrude from the shield and outer sheath assembly, respectively, during rotation and translation of the cutting tip. The alert may be presented to the user in one or more of audible signal(s), visual signal(s), tactile signal(s) and/or a combination of all types of signals. For example, referring to FIG. 19, the controller 2404 may send a visual alert signal to one or a plurality of light emitting diodes 2416 that are indicative of the shield configuration position, such as one color being indicative of a "shielded rotational orientation" and another color being indicative of an "extended rotational orientation." The controller 2404 may alternatively or additionally send an audible alert signal to a speaker 2424 through an optional audio amplifier 2426, and the speaker 2424 may produce different sounds (e.g., tone type, volume, etc.) indicative of whether the shield and/or shield drive mechanism being in one of a shielded configuration or an extended configuration.

As discussed above, the surgical device 2000 includes a position switch(es) 2376 or sensor(s) that determines the position(s) of the inner sheath assembly 542' and the cutting tip 534', including when the cutting tip the inner sheath assembly 542' and the cutting tip 534' are in their home position and the switch(es) 2376 or sensors produce and send corresponding cutting-tip position signals to the controller 2404. The controller 2404, in turn, produces and sends corresponding alert signals to the user and/or controls the operation of the surgical device 2000. For example, in order for the user to activate the surgical device 2000, it may be desirable for the inner sheath assembly 542' and the cutting tip 534' to be in their home position or another position prior to initiation of rotation and distal translation of the inner sheath assembly 542' and the cutting tip 534'. Similarly, it may be desirable to deactivate rotation and translation of the inner sheath assembly 542' and the cutting tip 534' upon the controller 2404 sensing that the inner sheath assembly 542' and the cutting tip 534' are in or not in certain positions. Accordingly, the controller 2404 may deactivate and/or allow activation of the cutting tip drive mechanism depending upon the position signal being indicative of the cutting tip being in at least one or more axial and/or rotational positions. And upon sensing axial and/or rotational position of the inner sheath assembly 542' and the cutting tip 534', the controller 2404 will produce corresponding alert signals, such as the one or more audible signal(s), visual signal(s), tactile signal(s) and/or a combination of all types of signals, similar to those discussed above. It shall be understood that "allowing activation" of the cutting tip drive mechanism means allowing (inhibiting interruption) of the flow of current from the power source to the trigger 2310 and/or motor 2360, and "inhibiting activation" or "deactivation" of the cutting tip drive mechanism means interrupting the flow of current from the power source to the trigger 2310 and/or motor 2360. The "inhibiting activation" or "deactivation" may be controlled by the controller 2404 either alone or in conjunction with other electrical components, such as a motor driver 2408. For example, the controller 2404 may directly control the motor driver 2308, which in turn is electrically coupled to and cooperates with the motor 2406, or the controller may send corresponding signals to the motor driver 2408 indicative of "inhibiting activation" or "deactivation."

The motor 2360 may include an encoder 2358, which monitors and controls the speed, position and rotational direction of the motor shaft 2364. The motor 2360 may include a current sensor and/or the control system 2400 may include a current sensor 2412 that monitors the motor current. For example, the motor 2360 adjusts the motor current in order to maintain a consistent rotational speed of the motor shaft 2364. As discussed above, when the acme nut 2372 contacts the means for limiting the axial or longitudinal movement of the acme nut 2372, the current supplied to the motor 2360 may increase. Upon the controller 2404 sensing and determining that the motor current exceeds a predetermined threshold, the supply of power to the motor 2360 is discontinued, thereby stopping and inhibiting further rotation and translation of the cutting tip drive mechanism and the inner sheath assembly 542' and the cutting tip 534'.

The controller 2404 may also include a module or logic that combines the shield position signals from the switches 2392a, 2392b (or sensor) indicative of the position and orientation of the shield and shield drive mechanism with the signals from the position switches 2376 (or sensor) indicative of the axial or rotational position of the inner sheath assembly 542' and the cutting tip 534'. Upon receiving such signals, the controller 2404 will produce corresponding alerts, allow activation of the cutting tip drive mechanism and/or deactivate the cutting tip drive mechanism. Examples of the controller's actions based upon the receipt of the individual or the combination of one or more signals are included in Table 1 below:

TABLE 1

| Shield Position Signal | Cutting Tip Position Signal After Calibration | Motor Current Signal | Alert Signal | Controller Action |
| --- | --- | --- | --- | --- |
| Position 1 (shield extended most distally) | At Home Position (cutting tip in its most proximal position) | Below Pre-Determined Threshold/Limit | Ready for Activation | Allow Activation of Cutting-Tip Drive Mechanism |
| Position 1 (shield extended most distally) | At Position Other than Home Position (cutting tip not in its most proximal position) | Below Pre-Determined Threshold/Limit | Ready for Activation | Allow Activation of Cutting-Tip Drive Mechanism |
| Position 1 (shield extended most distally) | At Position Other than Home Position | Below Pre-Determined Threshold/Limit | Continue Activation | Continue to Allow Activation of Cutting-Tip Drive Mechanism |
| Position 1 (shield extended most distally) | At Position Other than Home Position | At or Above Pre-Determined Threshold/Limit | Deactivated | Deactivate Cutting-Tip Drive Mechanism |
| Position 2 (shield partially extended distally and partially retracted proximally) | At Home Position (cutting tip in its most proximal position) | Below Pre-Determined Threshold/Limit | Ready for Activation | Allow Activation of Cutting-Tip Drive Mechanism |

TABLE 1-continued

| Shield Position Signal | Cutting Tip Position Signal After Calibration | Motor Current Signal | Alert Signal | Controller Action |
|---|---|---|---|---|
| Position 2 (shield partially extended distally and partially retracted proximally) | At Position Other than Home Position (cutting tip not in its most proximal position) | Below Pre-Determined Threshold/Limit | Ready for Activation | Allow Activation of Cutting-Tip Drive Mechanism |
| Position 2 (shield partially extended distally and partially retracted proximally) | At Position Other than Home Position | Below Pre-Determined Threshold/Limit | Continue Activation | Continue to Allow Activation of Cutting-Tip Drive Mechanism |
| Position 2 (shield partially extended distally and partially retracted proximally) | At Position Other than Home Position | At or Above Pre-Determined Threshold/Limit | Deactivated | Deactivate Cutting-Tip Drive Mechanism |
| Position 3 (shield fully retracted proximally) | At Home Position (cutting tip in its most proximal position) | Below Pre-Determined Threshold/Limit | Ready for Activation | Allow Activation of Cutting-Tip Drive Mechanism |
| Position 3 (shield fully retracted proximally) | At Position Other than Home Position (cutting tip not in its most proximal position) | Below Pre-Determined Threshold/Limit | Not Ready for Activation | Inhibit Activation and/or Deactivate Cutting-Tip Drive Mechanism |
| | At Position Other than Home Position | Below Pre-Determined Threshold/Limit | Continue Activation | Continue to Allow Activation of Cutting-Tip Drive Mechanism |
| | At Position Other than Home Position | At or Above Pre-Determined Threshold/Limit | Deactivated | Deactivate Cutting-Tip Drive Mechanism |

The controller 2404 may also include one or more modules that monitor and sense the remaining power and/or the voltage decay of the power source (e.g., battery) and the duration (time) of usage of the motor 2360. If the power and/or the voltage decay of the power source is below a predetermined threshold, then the controller 2404 limits the duration and/or use of the surgical device 2000 including producing and alert and/or deactivating the cutting tip drive mechanism. Similarly, if the motor is used for a period of time greater than the predetermined threshold, the controller 2404 produces and alert indicating that the time is nearing expiration and/or has expired, and/or the controller deactivates the cutting tip drive mechanism.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for removing an implanted object from a body vessel, the device comprising:
   an outer sheath;
   an inner sheath disposed within the outer sheath, the inner sheath comprising a cutting tip having a cutting surface;
   a cutting tip drive mechanism comprising a motor configured to rotate the cutting tip, wherein, upon actuation of the motor, the cutting tip rotates and translates longitudinally;
   a sensor, wherein the sensor provides a position signal indicative of a home position for the cutting tip drive mechanism; and
   a controller comprising a non-transitory computer-readable medium comprising instructions that, when executed, actuate the motor and calibrate a position of the motor based at least in part on the position signal received from the sensor while the motor is actuated,
   wherein the instructions cause the controller to rotate the motor in a first direction until the position signal indicating the home position for the cutting tip drive mechanism is received,
   wherein the instructions further cause the controller to rotate the motor in a second direction opposite the first direction until the position signal indicating the home position for the cutting tip drive mechanism is again received.

2. The device of claim 1, wherein the motor is set to a zero position when the position signal indicates that the cutting tip drive mechanism is in the home position after the motor is rotated in the second direction.

3. A device for removing an implanted object from a body vessel, the device comprising:
   an outer sheath;
   an inner sheath disposed within the outer sheath, the inner sheath comprising a cutting tip having a cutting surface;
   a cutting tip drive mechanism comprising a motor configured to rotate the cutting tip, wherein, upon actuation of the motor, the cutting tip rotates and translates longitudinally;
   a sensor, wherein the sensor provides a position signal indicative of a home position for the cutting tip drive mechanism; and
   a controller comprising a non-transitory computer-readable medium comprising instructions that, when executed, actuate the motor and calibrate a position of the motor based at least in part on the position signal received from the sensor while the motor is actuated,
   wherein the instructions cause the controller to:
     rotate the motor in a first direction;
     discontinue rotation in the first direction if the position signal indicating the home position for the cutting tip drive mechanism is received; and
     rotate the motor in a second direction opposite the first direction if the position signal indicting the home position for the cutting tip drive mechanism is not received.

4. A device for removing an implanted object from a body vessel, the device comprising:
   an outer sheath;
   an inner sheath disposed within the outer sheath, the inner sheath comprising a cutting tip having a cutting surface;
   a cutting tip drive mechanism comprising a motor configured to rotate the cutting tip, wherein, upon actuation of the motor, the cutting tip rotates and translates longitudinally;
   a sensor, wherein the sensor provides a position signal indicative of a home position for the cutting tip drive mechanism; and
   a controller comprising a non-transitory computer-readable medium comprising instructions that, when executed, actuate the motor and calibrate a position of the motor based at least in part on the position signal received from the sensor while the motor is actuated,
   wherein the cutting tip drive mechanism further comprises a current sensor, wherein the current sensor produces a current signal indicative of the motor exceeding a predetermined current threshold.

5. The device of claim 4, wherein the controller initially rotates the motor in a first direction, and then discontinues rotating of the motor in the first direction when the current signal indicates that the current threshold is exceeded.

6. The device of claim 5, wherein controller rotates the motor in a second direction opposite the first direction after the current signal indicates that the current threshold is exceeded.

7. The device of claim 6, wherein the controller continues to rotate the motor in the second direction until the sensor produces the position signal.

8. A device for removing an implanted object from a body vessel, the device comprising:
   an outer sheath;
   an inner sheath disposed within the outer sheath, the inner sheath comprising a cutting tip having a cutting surface;
   a cutting tip drive mechanism comprising a motor configured to rotate the cutting tip, wherein, upon actuation of the motor, the cutting tip rotates and translates longitudinally;
   a sensor, wherein the sensor provides a position signal indicative of a home position for the cutting tip drive mechanism; and
   a controller comprising a non-transitory computer-readable medium comprising instructions that, when executed, actuate the motor and calibrate a position of the motor based at least in part on the position signal received from the sensor while the motor is actuated,
   wherein the controller discontinues rotating the motor in a first direction and initiates rotating the motor in a second direction opposite the first direction.

9. A device for removing an implanted object from a body vessel, the device comprising:
   a sheath comprising a cutting tip having a cutting surface;
   a cutting tip drive mechanism comprising a motor configured to rotate the cutting tip, wherein, upon actuation of the motor, the cutting tip rotates and translates longitudinally within the sheath;
   a sensor, wherein the sensor provides a position signal indicating that the cutting tip drive mechanism is in a home position within the sheath; and
   a controller comprising a non-transitory computer-readable medium comprising instructions that, when executed, cause the controller to:
     rotate the motor in a first direction;
     discontinue rotation of the motor if the position signal indicating the home position for the cutting tip drive mechanism is received, and otherwise rotate the motor in a second direction opposite the first direction until the position signal indicating the home position for the cutting tip drive mechanism is received; and after the position signal indicating that the home position for the cutting tip drive mechanism is received, calibrating cutting tip drive mechanism so that a zero position of the motor corresponds to the current position of the cutting tip drive mechanism.

10. The device of claim 9, wherein the cutting tip translates within the sheath in a first longitudinal direction when the motor rotates in the first direction and in a second longitudinal direction opposite the first longitudinal direction when the motor rotates in the second direction opposite the first direction.

11. The device of claim 9, further comprising a current sensor configured to provide an alert signal to the controller when a motor current exceeds a threshold.

12. The device of claim 11, wherein the rotation of the motor is discontinued when the controller receives the alert signal from the current sensor.

13. The device of claim 9, wherein the cutting tip translates within the sheath in a first longitudinal direction when the motor rotates in the first direction and in a second longitudinal direction opposite the first longitudinal direction when the motor rotates in the second direction opposite the first direction.

14. A device for removing an implanted object from a body vessel, the device comprising:

a sheath comprising a cutting tip having a cutting surface;

a cutting tip drive mechanism comprising a motor configured to rotate the cutting tip, wherein, upon actuation of the motor, the cutting tip rotates and translates longitudinally within the sheath;

a current sensor configured to provide an alert signal when a motor current exceeds a threshold;

a sensor configured to provide a position signal indicating that the cutting tip drive mechanism is in a home position within the sheath; and a controller comprising a non-transitory computer-readable medium comprising instructions that, when executed, cause the controller to:

rotate the motor in a first direction until either the position signal is received from the sensor or the alert signal is received from the current sensor;

if the alert signal from the current sensor is received, rotate the motor in a second direction opposite the first direction until the position signal is received from the sensor; and after the position signal indicating that the home position for the cutting tip drive mechanism is received from the sensor, calibrating the cutting tip drive mechanism so that a zero position of the motor corresponds to the current position of the cutting tip drive mechanism.

* * * * *